US011075065B2

(12) United States Patent
Pyun

(10) Patent No.: US 11,075,065 B2
(45) Date of Patent: Jul. 27, 2021

(54) SAMPLE PLATE, METHOD OF FABRICATING THE SAME AND MASS SPECTROMETER ANALYSIS BY USING THE SAME

(71) Applicant: UNIVERSITY-INDUSTRY FOUNDATION (UIF), YONSEI UNIVERSITY, Seoul (KR)

(72) Inventor: Jae-Chul Pyun, Seoul (KR)

(73) Assignee: UNIVERSITY-INDUSTRY FOUNDATION (UIF), YONSEI UNIVERSITY, Seoul (KR)

( * ) Notice: Subject to any disclaimer, the term of this patent is extended or adjusted under 35 U.S.C. 154(b) by 277 days.

(21) Appl. No.: 15/840,041

(22) Filed: Dec. 13, 2017

(65) Prior Publication Data

US 2018/0166267 A1   Jun. 14, 2018

(30) Foreign Application Priority Data

Dec. 13, 2016 (KR) .................. 10-2016-0169954
Nov. 6, 2017 (KR) .................. 10-2017-0147001

(51) Int. Cl.
*G01N 33/00* (2006.01)
*H01J 49/04* (2006.01)
*G01N 33/68* (2006.01)

(52) U.S. Cl.
CPC ...... *H01J 49/0418* (2013.01); *G01N 33/6851* (2013.01); *H01J 49/049* (2013.01); *G01N 2560/00* (2013.01)

(58) Field of Classification Search
CPC .................................. H01J 49/0418

USPC .......................................... 436/89
See application file for complete search history.

(56) References Cited

U.S. PATENT DOCUMENTS

2016/0027631 A1* 1/2016 Naya .................. G01N 21/658
                                                                356/72

FOREIGN PATENT DOCUMENTS

KR    10-2012-0095638       8/2012
KR       20120095638 A  *  8/2012  .......... H01J 49/0418

OTHER PUBLICATIONS

Kim et al. "Nylon nanoweb with TiO2 nanoparticles as a solid matrix for matrix-assisted laser desorption/ionization time-of-flight mass spectrometry" Rapid Commun. Mass Spectrom. 2014, 28, 2427-2436 (Year: 2014).*
Blacken et al. "Reactive Landing of Gas-Phase Ions as a Tool for the Fabrication of Metal Oxide Surfaces for In Situ Phosphopeptide Enrichment" J Am Soc Mass Spectrom 2009, 20, 915-926 (Year: 2009).*
Translation of KR20120095638 obtained Jul. 16, 2020 (Year: 2020).*
Office Action dated Feb. 13, 2019 corresponding to Korean Patent Application No. 10-2017-0147001, 5 pages.

* cited by examiner

*Primary Examiner* — Christine T Mui
*Assistant Examiner* — Emily R. Berkeley

(57) ABSTRACT

The present disclosure relates to a sample plate for laser desorption/ionization mass spectrometry comprising a substrate including a surface corrosion layer, and the surface corrosion layer constitutes at least a portion of the photoreaction catalyst layer, and a photocatalytic catalyst layer including a metal oxide formed on the substrate, wherein a sample to be analyzed is disposed on the photocatalytic catalyst layer.

7 Claims, 28 Drawing Sheets

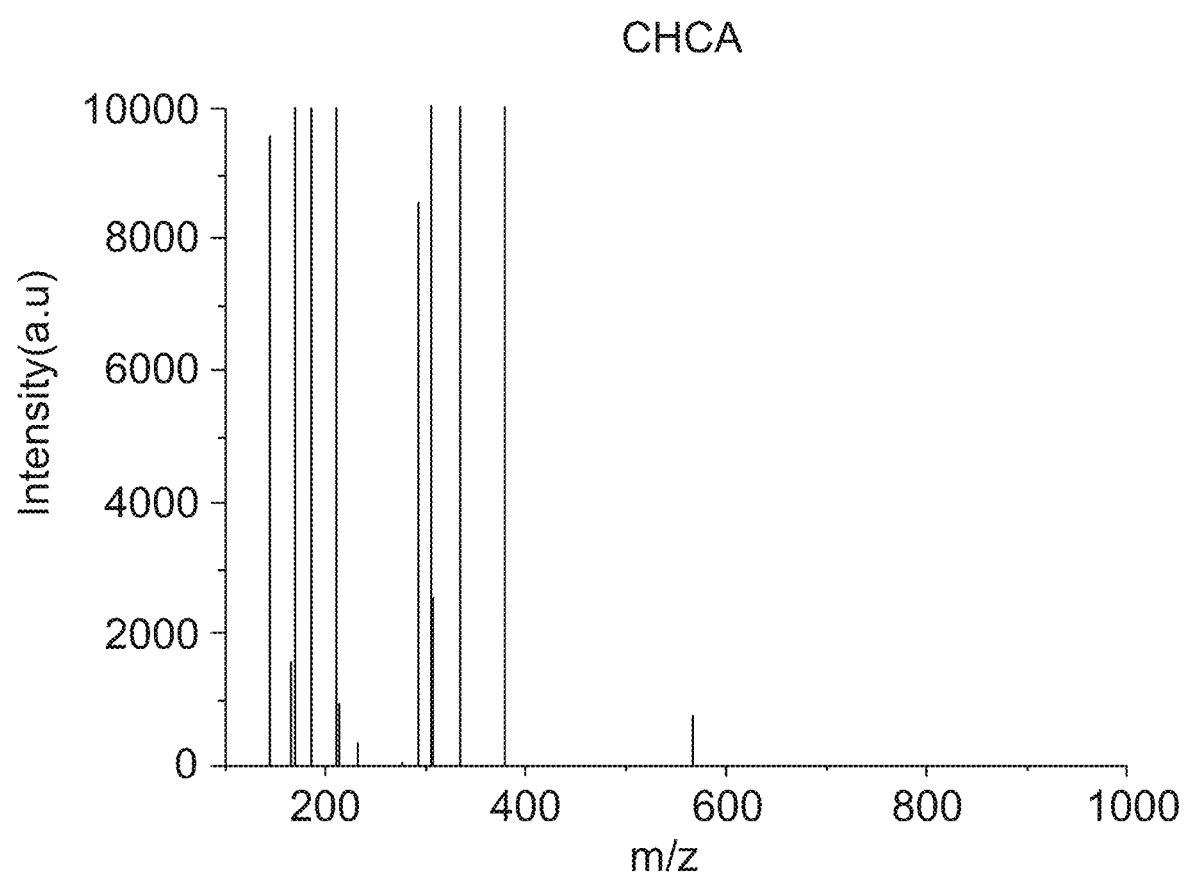

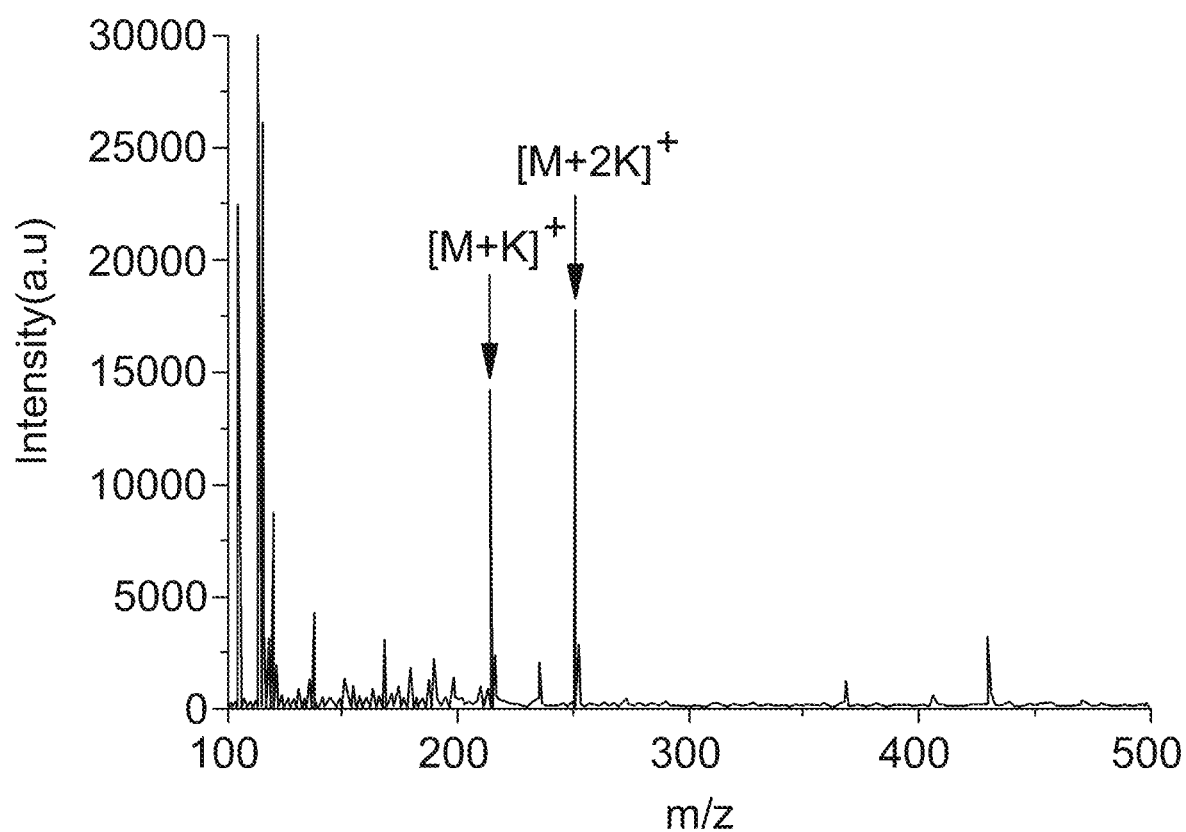

R4K peptide 1 mg/ml(770.51 g/mol)

Primary sequence fragment

R4K peptide 1 mg/ml(770.51 g/mol)

Primary sequence fragment

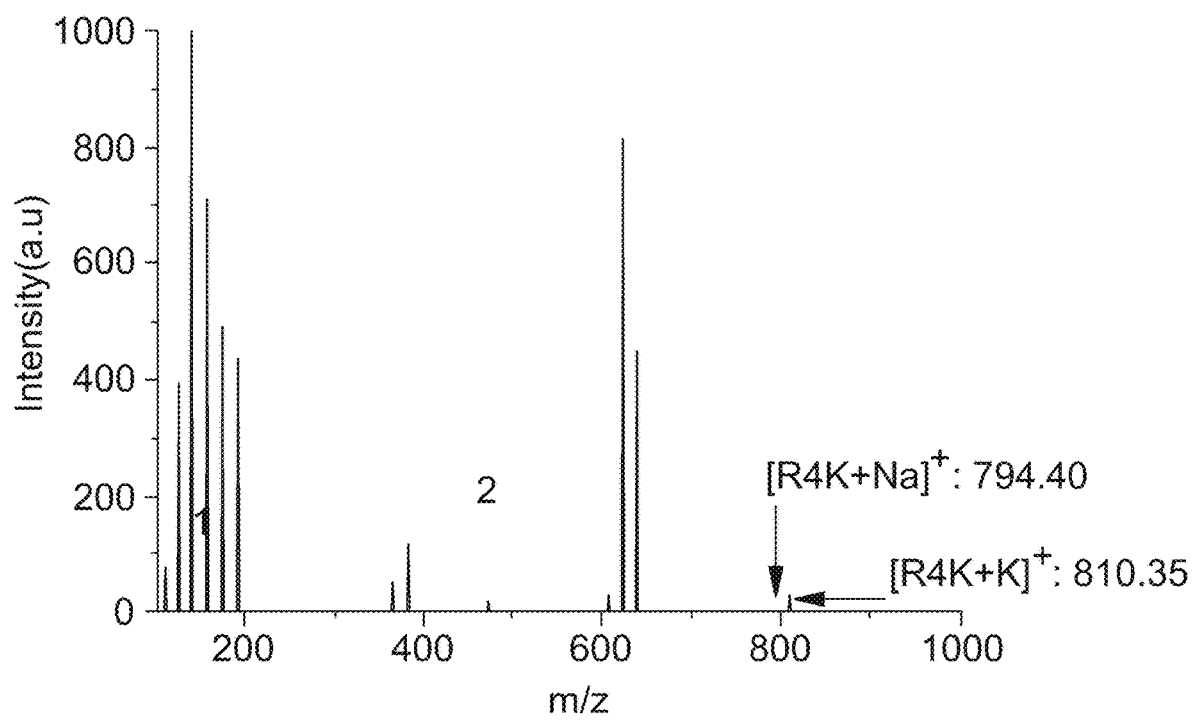

GHP9 peptide 1 mg/ml(1007.18 g/mol)

BPA peptide 1 mg/ml (1395.56 g/mol)

- Sample 1(primary sequence : GYHPQRK, 884.46 g/mol)

before ultraviolet irradiation in CHCA $[HPQ-1+H]^+$: 886.26 after ultraviolet irradiation

- Sample 2(primary sequence : KRHPQYG, 884.46 g/mol)

before ultraviolet irradiation in CHCA after ultraviolet irradiation

• Sample 3(primary sequence : RYHPQGK, 884.46 g/mol)

before ultraviolet irradiation in CHCA

[HPQ-3+H]$^+$: 886.26 after ultraviolet irradiation

Unidirectional 500

Unidirectional 500

| | Surface area (µm²) |
|---|---|
| 500x500 | 2415.0334 |
| 400x400 | 2177.2148 |
| 320x320 | 2131.0749 |
| 180x180 | 2177.9703 |

SAMPLE PLATE, METHOD OF FABRICATING THE SAME AND MASS SPECTROMETER ANALYSIS BY USING THE SAME

CROSS-REFERENCE TO RELATED APPLICATION

This application claims priority of Korean Patent Application No. 10-2016-0169954, filed on Dec. 13, 2016, and priority of Korean Patent Application No. 10-2017-0147001, filed on Nov. 6, 2017, in the KIPO (Korean Intellectual Property Office), the disclosure of which is incorporated herein entirely by reference.

BACKGROUND OF THE INVENTION

Field of the Invention

The present invention relates to a technology for mass spectrometry on an analyte, and more particularly, a sample plate for mass spectrometry, method for fabricating the same and mass spectrometry analysis by using the same.

Description of the Related Art

Generally, a mass spectrometer is an analytical instrument for measuring the mass of an analyte, for example, a chemical compound to be analyzed. The analyte is charged and ionized, and the mass-to-charge (m/z) is measured to determine the molecular weight of the compound. As the methods for ionizing the analyte, an electron ionization using an electron beam, high-speed atom collision, laser irradiation, and injection method of an analyte into an electric field are already widely-known.

As a typical mass spectrometer, a MALDI-TOF MS Apparatus (Matrix-Assisted Laser Desorption Ionization Time Flight Mass Spectroscopy) mixes an organic matrix for assisting ionization of a sample to be analyzed with the sample, arrange the sample on a target of the analyzing device and then irradiates laser to the sample to be analyzed. Then, mass analysis is performed using the property that the sample to be analyzed is easily ionized with the assist of the organic matrix. The MALDI-TOF mass spectrometry method has a high sensitivity, and thus it is possible to analyze a sample to be analyzed at the level of pepto-mol, and it is advantageous in that the phenomenon of fragmentation of a compound to be analyzed at the time of ionization can be greatly reduced. MALDI-TOF mass spectrometry using a laser is effective for mass spectrometry of large molecular biochemicals such as proteins and nucleic acids and thus, recently, this method is being applied widely. Generally, in the case of the MALDI-TOF mass spectrometry, when the analytical sample is ionized, the valence number of the ion of the sample to be analyzed is +1 or +2, which is an easy method for measuring the molecular weight of the sample molecule before ionization.

However, the MALDI-TOF mass spectrometry has a demerit that different organic matrix materials must be determined according to the type of the sample to be analyzed since the analyte is ionized using the organic matrix. In addition, a commonly used organic matrix material has a molecular weight of several hundred Da. When the molecular weight of the sample to be analyzed is similar to or smaller than the molecular weight of the organic matrix material, materials originated from the organic matrix may be reflected in the mass peak of the mass spectrometry spectrum. Therefore, it has limitations that are difficult to apply for mass spectrometry of samples of analytes of several hundred Da levels.

SUMMARY OF THE INVENTION

The present invention provides a sample plate applicable to mass spectrometry and capable of performing reliable mass spectrometric analysis on a sample having a low molecular weight.

Another object of the present invention is to provide a method of manufacturing a sample plate which can easily produce a sample plate having the above advantages.

It is another object of the present invention to provide a mass spectrometry method using the sample plate having the above advantages.

Another object of the present invention is to provide a method for analyzing an amino acid sequence capable of identifying or quantifying a pap target compound using the sample plate.

According to an embodiment of the present invention, there is provided a sample plate for laser desorption/ionization mass spectrometry comprising: a substrate; and a photocatalytic catalyst layer comprising a metal oxide formed on the substrate, wherein a sample to be analyzed is disposed on the photocatalytic catalyst layer. The photoreaction catalyst layer may be provided with a sample plate including a surface corrosion layer of the substrate. The metal oxide may comprise an oxide layer on the surface of the substrate. The metal oxide may be at least any one of titanium (Ti), tantalum (Ta), tin (Sn), tungsten (W), zinc (Zn), vanadium (V), ruthenium (Ru), iridium (Ir) Or an oxide of any one of the metals. The metal oxide may have a porous structure and may have a nano scale structure having a fibrous shape, a wire shape, a needle shape, a film shape, a columnar shape, or a combination thereof. The sample to be analyzed forms fragments by photolysis reaction by ultraviolet irradiation incident on the photoreaction catalyst layer, and mass analysis of the fragments can be performed.

According to another embodiment of the present invention, there is provided a method of manufacturing a sample plate for laser desorption/ionization mass spectrometry, comprising the steps of: providing a substrate comprising metal atoms constituting a photoreaction catalyst layer; and exposing the surface of the metal-containing substrate to an oxidizing solvent to oxidize the metal while corroding the surface of the substrate to form a photoreaction catalyst layer containing an oxide of the metal Can be. The metal atoms may include tantalum (Ta), tin (Sn), tungsten (W), zinc (Zn), vanadium (V), ruthenium (Ru), iridium (Ir). By etching the surface of the substrate, the photoreaction catalyst layer can have a porous nano scale structure. The step of forming the photoreaction catalyst layer comprises the steps of: immersing the substrate in the oxidizing solvent to form an oxide of the metal on the surface of the substrate; and cleaning the substrate on which the oxide of the metal is formed. The oxidizing solvent may include a metal corroding material such as KOH, NaOH, and the like.

According to still another embodiment of the present invention, there is provided a method of manufacturing a light emitting device, comprising the steps of: providing a sample plate including the photoreactive catalyst layer according to the first aspect; loading a sample to be analyzed on the photoreactive catalyst layer; irradiating the sample to be analyzed with ultraviolet rays to induce a photodecomposition reaction of the sample to be analyzed; and performing mass spectrometry by laser desorption/ionization on the sample to be analyzed that has undergone the photolysis reaction. The sample to be analyzed is dispersed in a dispersion solvent and provided on the photoreaction catalyst layer, and the ultraviolet ray is irradiated to the dispersion solution of the sample to be analyzed to induce the photolysis reaction. The sample to be analyzed includes an organic molecular compound, and the organic molecular compound can be fragmented by the photolysis reaction. The sample to be analyzed includes different kinds of organic molecular compounds, and the organic molecular compounds can be specifically fragmented by the photolysis reaction to identify the organic molecular compounds.

According to another embodiment of the present invention, there is provided a method of manufacturing a light emitting device, comprising the steps for: providing a sample plate including a photoreactive catalyst layer including a porous metal oxide; loading a peptide compound to be analyzed on the photoreaction catalyst layer; irradiating the peptide compound with ultraviolet light to form peptide fragments by photodecomposition of the peptide compound; irradiating a laser onto the photoreaction catalyst layer to desorb and ionize the peptide fragments from the photoreaction catalyst layer; and analyzing the molecular weight of the peptide compound before the ultraviolet irradiation and the molecular weight of the ionized peptide fragments to determine the amino acid sequence of the peptide compound. The sample to be analyzed may comprise a mixture of different peptide compounds. The photoreaction catalyst layer may be formed of at least one of titanium, tantalum, tungsten, zinc, vanadium, ruthenium, iridium, Or an oxide of at least one of the metals. The photoreactive catalyst layer may have a porous nano scale structure.

BRIEF DESCRIPTION OF THE DRAWINGS

The above and other features and advantages will become more apparent to those of ordinary skill in the art by describing in detail exemplary embodiments with reference to the attached drawings, in which:

FIG. 3B is a graph showing the results of mass spectrometry for a sample plate using an organic matrix containing α-cyano-4-hydroxycinnamic acid (hydroxycinnamic acid; CHCA) according a comparison examples.

FIGS. 4A to 4D are graphs showing mass spectrometry results of various organic molecular compounds using a sample plate including a $TiO_2$ nano scale structure photoreaction catalyst layer according to an embodiment of the present invention.

FIG. 6B and FIG. 6C are graphs showing mass spectrometry results before and after ultraviolet irradiation using $TiO_2$ particles according to comparative examples.

In the following description, the same or similar elements are labeled with the same or similar reference numbers.

DETAILED DESCRIPTION

Figure 1A:
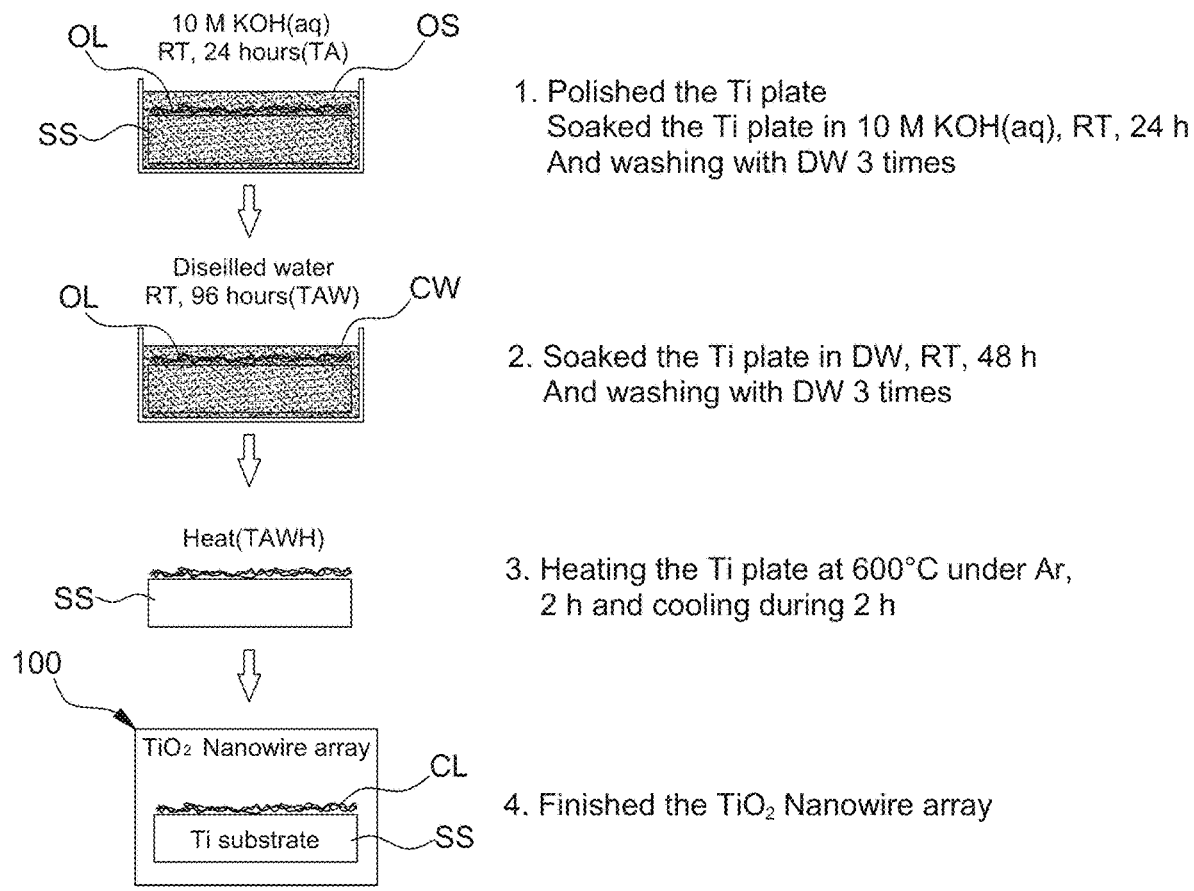
FIG. 1A is a diagram schematically illustrating a method of manufacturing a sample plate including a photoreaction catalyst layer according to an embodiment of the present invention.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

As used herein, the term, "peptide compound" refers to a short protein having 40 or fewer amino acids constituting it. In general, the sequence of the amino acid, i.e., the sequence of the joined amino acids, refers to the amino acid bonding order from the amine terminus (N-terminus) to the carboxyl terminus (C-terminus) of the peptide.

In the embodiments of the present invention, the sample to be analyzed is fragmented by the photoreaction catalyst layer of the sample plate, and tandem mass analysis can also be performed in the MALDI-TOF mass analysis. For example, in order to analyze the amino acid sequence of a peptide compound, mass fractionation of fragmented peptide fragments using the above-described photoreaction catalyst layer yields peptide fragments in which amino acids are removed one by one from the amine terminus (N-terminus) can be measured. For example, when a peptide compound composed of five amino acids is analyzed similarly to the tandem mass method, the molecular weight of the whole peptide compound composed of the above five amino acids can be measured through mass spectrometry. Then, when irradiating the photocatalytic catalytic layer with ultraviolet rays to induce a photodecomposition reaction of the peptide compound, so that a peptide fragment composed of four, three and/or two amino acids can be formed, measuring the molecular weight thereof, and comparing and analyzing the peptides, the sequence of the amino acid from the N-terminal to the C-terminal can be determined. The method of analyzing the amino acid sequence for the above-mentioned peptide substance is only illustrative and the present invention is not limited thereto.

Figure 1B:
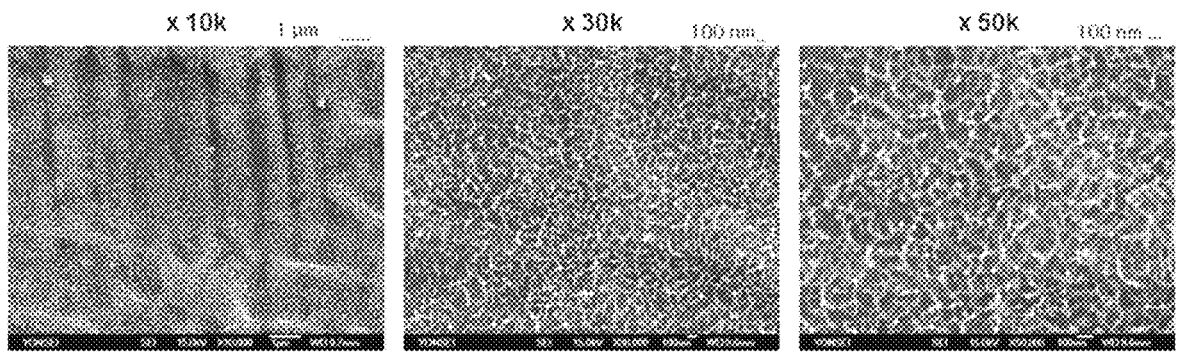
FIG. 1B shows scanning electron microscope images of a microstructure of the photoreaction catalyst layer on the unpolished substrate.
Figure 1C:
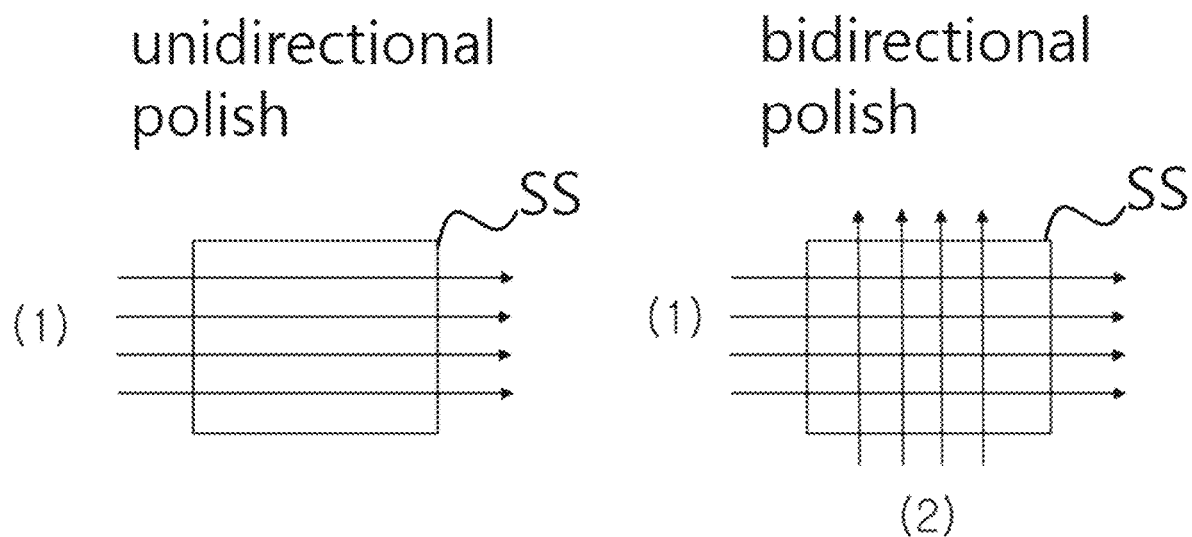
FIG. 1C shows polishing process for various type of stripe pattern on the substrate.

FIG. 1A is a schematic view illustrating a method of manufacturing a sample plate 100 including a photoreaction catalyst layer CL according to an embodiment of the present invention. FIG. 1B is a scanning electron microscope image measuring a microscopic structure of a photoreaction catalyst layer CL. FIG. 1C shows a method of forming a uni-directional stripe pattern and bi-directional stripe pattern on the substrate SS.

Referring to FIG. 1A, a substrate SS on which a photoreaction catalyst layer CL is to be formed is first prepared for the production of a sample plate 100 having a photoreaction catalyst layer CL formed thereon. In one embodiment, the substrate SS may include metal atoms, some or all of which constitute a photoreaction catalyst layer. In FIG. 1A, a substrate SS including metal atoms constituting a photoreaction catalyst layer is illustrated. In this case, a photoreaction catalyst layer can be formed by forming a reaction layer directly from the surface of the substrate SS. For example, when the photoreaction catalyst layer CL comprises a metal oxide, the surface or the entire surface of the substrate SS may include a metal of the metal oxide. In addition, the photoreaction catalyst layer CL can be formed by oxidizing some portions of the surface.

The substrate SS may be, for example, a titanium substrate. In another embodiment, the substrate SS may comprise at least one of tantalum (Ta), tin (Sn), tungsten (W), zinc (Zn), vanadium (V), ruthenium (Ru), iridium (Ir), iron (Fe) or an alloy thereof.

In one embodiment, the substrate SS may be polished to adjust a roughness of a surface of the substrate SS to control a surface area exposed to a below-mentioned oxidizing solvent OS for etching the surface of the substrate SS. The surface roughness of a diamond sand having, for example, 180, 320, 400, and 500 mesh may be used for the polishing process. The polishing may be carried out by mounting each sandpaper on a rotary grinder and pressing the substrate by a rotary plate of the rotary grinder while rotating the rotary plate at a speed of 100 rpm. The polishing process may provide, for example, uni-directional stripe pattern and bi-directional stripe pattern (or called as cross stripe pattern) on the polished surface of the substrate SS. The polishing process may be performed for a few minutes and a few hours, for example, 5 minutes. In the case of the bi-directional stripe pattern, the substrate may be polished for 5 minutes in one direction for a first stripe pattern. Then the substrate may be rotated 90 degrees for additional polishing for 5 minutes to form a second stripe pattern crossing the first pattern.

In one embodiment, the surface of the substrate SS may be exposed to an oxidizing solvent (OS) to corrode the surface of the substrate SS. For example, the substrate SS may be immersed in the oxidizing solvent (OS) and kept at room temperature for about 24 hours to corrode the surface. In one embodiment, a process for forming the fore-mentioned polishing process on the surface of the substrate SS may be further performed before immersing the substrate SS in the oxidizing solvent OS.

The oxidizing solvent OS may be, for example, alkaline solution which causes corrosion of metal such as KOH and NaOH. The concentration of the oxidizing solvent OS may be 10 M falling within the concentration range of 2 M to 20 M (see step 1 of FIG. 1A). The present invention is not limited by the concentration of the oxidizing solvent and can be variously selected depending on the kind and characteristics of the analyte for mass analysis. The oxidation reaction may proceed on the surface of the substrate SS during the corrosion of the surface of the substrate SS by the oxidizing solvent OS to form the oxide layer OL.

Thereafter, the substrate SS may be cleaned by using a cleaning liquid CW such as alcohol or distilled water DW. For example, the substrate SS may be immersed in the cleaning liquid CW for, for example, about 48 hours to absorb the cleaning liquid CS into the surface layer of the corroded substrate SS, may be repeated one or more times, for example three times (see step 2 of FIG. 1A). In this process, the oxidizing solvent remaining on the surface of the titanium substrate (SS) may be replaced with the cleaning liquid.

Since the surface of the substrate SS, which has been corroded by the oxidizing solvent, has porosity with nano scale pores, it is necessary to expose the corroded substrate SS for a sufficient time in the cleaning liquid CW. In one embodiment, the substrate SS may be immersed in a cleaning liquid CW at room temperature (RT) for 48 hours, and the cleaning process may be performed about three times (see step 2 in FIG. 1A).

Thereafter, the cleaned substrate may be heat-treated (see step 3 in FIG. 1A). The heat treatment may be performed within a temperature range of about 200° C. to 1,200° C. However, the present invention is not limited thereto. The temperature of the heat treatment may be set such that the surface layer of the corroded substrate (SS) can be adjusted to have a crystalline or microstructure suitable for inducing the reaction. In one embodiment, the substrate SS can be heat treated at about 600° C. for a predetermined time (e.g., 2 hours) in an inert gas atmosphere, for example, an Ar gas atmosphere.

Thereby, the sample plate 100 on which the light reaction catalyst layer CL may be formed on the surface of the substrate SS can be provided. When the substrate SS is a titanium substrate, a $TiO_2$ nano-array layer may be formed as a photoreaction catalyst layer CL.

In the above-described embodiment, the surface of the substrate SS is modified to obtain the photoreaction catalyst layer CL. In another embodiment, when the substrate SS does not include or is independent of the elements of the photoreaction catalyst layer CL, a metal layer containing a metal element of the photoreaction catalyst layer CL may be formed on the surface of the substrate SS. The photoreaction catalyst layer CL may be formed from the metal layer by performing the steps 1 to 3 shown in FIG. 1A.

In another example, the photoreaction catalyst layer CL may be synthesized by a dry vapor deposition process such as chemical vapor deposition, physical vapor deposition, or atomic layer deposition on a substrate SS on which a metal catalyst layer of a dot array type may be formed, or by a wet film forming method such as a sol-gel method for forming a nano scale structure.

With respect to the precursor material for synthesis, well-known techniques may be taken into consideration and the present invention is not limited thereto. However, it is preferable that in the case of forming the light reaction catalyst layer CL by the wet etching method described with reference to FIG. 1A, the metal catalyst layer CL of a nano scale structure shape can be easily formed by acquiring a porous surface layer by corrosion without forming the metal catalyst layer CL.

The above-described photoreaction catalyst layer CL may be formed of a material which does not directly participate in the photolysis reaction of the organic molecular compound as the analyte but accelerates the photolysis of the organic molecular compound. In one embodiment, the photoreaction catalyst layer CL further includes at least any one of titanium (Ti), tantalum (Ta), tin (Sn), tungsten (W), zinc (Zn), vanadium (V), ruthenium Ir) and iron (Fe).

The photoreaction catalyst layer CL further includes at least any one of gold (Au), silver (Ag), platinum (Pt), silicon (Si), germanium (Ge) and gallium (Ga) on the metal oxide or on the inside thereof. Such doping of the impurities may be effective in controlling the frequency of the light source for the photoreaction of the organic molecular compound.

Preferably, the photoreaction catalyst layer CL may include titanium oxide ($TiO_2$) having an anatase crystal structure. The titanium oxide ($TiO_2$) is relatively inexpensive as compared with other metal oxides, is smoothly supplied, is not photo-corrosive, and is photoactivated by short-wavelength light irradiation including ultraviolet rays having a band gap of 3.2 eV of about 380 nm or less, thereby increasing the efficiency of the plasma display panel.

The surface of the photoreaction catalyst layer CL may have a nano scale structure according to the above corrosion method. The nano scale structure is porous and may have a fibrous shape, a wire shape, a needle shape, a film shape, a columnar shape, or a combination thereof, and may be patterned by photolithography or a shadow masking method.

In FIG. 1a, the light reaction catalyst layer CL is formed in a form of an array on the substrate SS. The nano scale structures of titanium oxide ($TiO_2$) constituting the photoreaction catalyst layer CL shown in FIG. 1a may be patterned in the form of a spot having a diameter of 1 mm. For example, the size of the substrate SS is about 3 cm×3 cm, and the spots of nano scale structures of titanium oxide ($TiO_2$) formed on the substrate SS may be plural.

The nano scale structure of the photoreaction catalyst layer CL formed on the substrate SS may form the above-described porous structure. As illustrated in FIG. 1B, a nano scale structure having a nano wire structure may be formed in the photoreactive catalyst layer CL of $TiO_2$.

Figure 2:
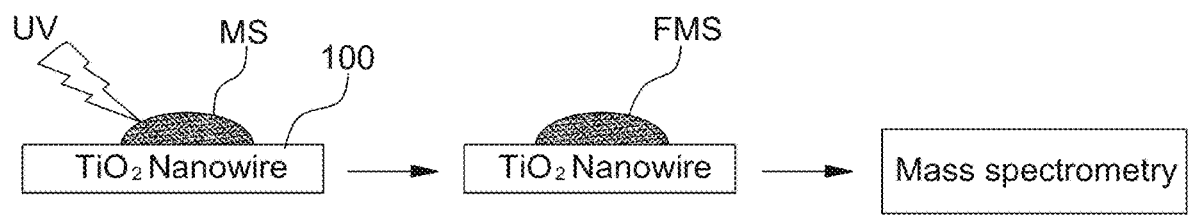
FIG. 2 is a diagram showing spectrometry method using a photoreaction catalyst layer according to an embodiment of the present invention.

FIG. 2 is a view showing a mass spectrometry using a photoreaction catalyst layer CL according to an embodiment of the present invention.

Referring to FIG. 2, a sample to be analyzed (or called as analyte; MS) may be loaded on a sample plate 100 for analysis of the sample to be analyzed. The sample to be analyzed may be an organic molecular compound. The organic molecular compound may be dispersed in a suitable dispersion solvent and provided on the photoreaction catalyst layer (see CL in FIG. 1A). The dispersion solvent may be water, acetonitrile, methanol, ethanol, or the like, or a mixture thereof, and a compound having a carboxyl group such as trifluoroacetic acid (a substance used as a source of H+ when ionizing the analyte) may be added. The dispersion solvent may be variously selected depending on the kind of the organic molecular compound to be analyzed, and the present invention is not limited to the exemplified solution.

When the photoreactive catalyst layer CL may be formed in the form of a plurality of patterned spot arrays as described above, a dispersion solution MS in which organic molecular compounds are dispersed in each photoreaction catalyst layer (CL) spot may be provided. For example, a dispersion solution of one microliters of the organic molecular compound may be spotted on a nano scale structure spot of the $TiO_2$ light reaction catalyst layer (CL).

Thereafter, ultraviolet rays (UV) may be irradiated to the dispersed solution MS of the loaded organic molecular compound to induce photodecomposition reaction of the organic molecular compound, for example, fragmentation reaction of organic molecules. When the organic molecular compound is a peptide substance, peptide fragments can be formed through photolysis reaction by ultraviolet (UV).

For the photolytic reaction, for example, a UV exposure apparatus having a wavelength of 254 nm and an intensity of 23 $mW/cm^2$ may be used. The sample plate 100 is located below a predetermined position from the UV exposure apparatus, and then UV irradiation is performed for 30 seconds so that the photolytic reaction of the organic molecular compound (MS), for example fragmentation, can be induced. When the photolysis reaction of the organic molecular compound MS is completed, the sample plate 100 can be dried. In FIG. 2, the reference character "FMS" denotes an organic molecular compound where the photolysis reaction is completed.

Laser desorption/ionization mass spectrometry may be performed on the organic molecular compound on which the photodegradation reaction has been completed on the dried sample plate 100, for example, using a mass spectrometer of Microflex model of Bruker. The mass spectrometer may be a mass spectrometer for MALDI-TOF analysis. In one embodiment, the reflector of the mass spectrometer may be set to a positive mode and the power of the laser may be adjusted to a level of several to several tens of percent based on the peak power, and the gain value of the detector can be properly adjusted.

In the MALDI-TOF mass spectrometry according to the embodiment of the present invention, when a laser beam is irradiated onto the surface of the sample plate 100, at least a part of the organic molecule fragments formed by the photolysis reaction are ionized, and the ionized organic molecule fragments pass through the flight tube of the MALDI-TOF mass spectrometer after being accelerated by an electric field. The ionized organic molecule fragments that have passed through the flight tube collide with the detector and the mass analyzer calculates the mass of organic molecular debris by calculating the time it takes for the ionized sample to impact the detector from the surface of the sample plate 100.

In the case of conventional MALDI-TOF mass spectrometry, it is necessary to mix the organic molecular compound and the organic matrix for desorption and ionization of the organic molecular compound to be analyzed. In this case, since the mass peak due to the organic matrix is observed as a noise signal having no reproducibility, when the organic molecular compound is a low molecular weight organic molecular compound having m/z of 500 or less, it is getting difficult to separate the mass peak and the organic molecular compound based on the organic matrix and thereby, signal measurement of the low molecular weight organic molecular compound using the organic matrix becomes almost impossible. However, the sample plate according to an embodiment of the present invention induces a photodegradation reaction such as fragmentation of an organic molecular compound by simply loading an organic molecular compound on a photoreaction catalyst layer without an organic matrix and irradiating ultraviolet rays, Desorption and ionization are induced by laser irradiation so that mass spectrometry signals of other substances having a low molecular weight such as the organic matrix are not generated in the mass spectrometric analysis.

As a result, according to the embodiment of the present invention, noise is not detected in a low molecular region having an m/z value of 500 or less, unlike the conventional MALDI-TOF mass spectrometry using an organic matrix. Therefore, organic molecule compounds having low molecular weight, for example, peptides as well as common organic molecule compounds can be effectively detected.

Figure 3A:
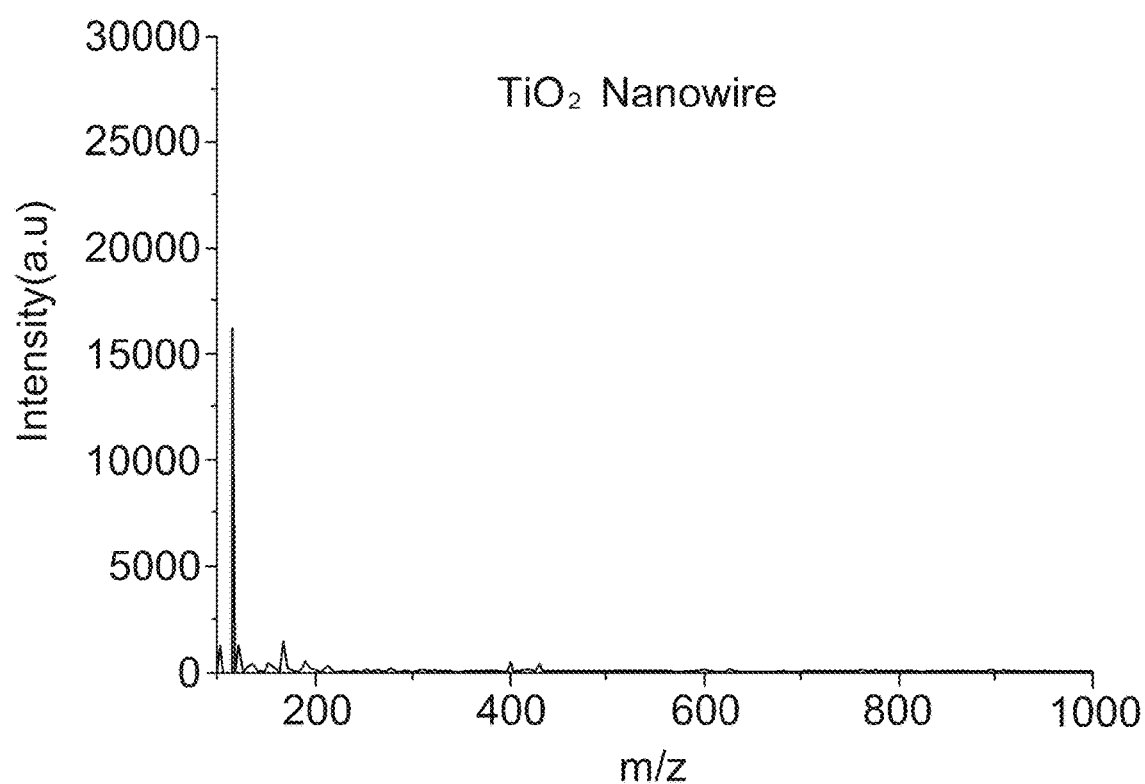
FIG. 3A is a graph showing the results of mass spectrometry for a bare sample plate according to an embodiment of the present invention.

FIG. 3A is a graph showing the results of mass spectrometry for a bare sample plate according to an embodiment of the present invention, and FIG. 3b is a graph showing the results of mass spectrometry for a sample plate using an organic matrix including α-cyano-4-hydroxycinnamic acid (hydroxycinnamic acid; CHCA) according to the comparison example.

Referring to FIG. 3A, a bare sample plate having a photocatalytic catalyst layer of $TiO_2$ according to an embodiment of the present invention does not generate a mass peak when there is no sample to be analyzed. Particularly, it should be noted that there is no mass peak in the region of 500 m/z or less. Unlike this fact, referring to FIG. 3B, in the case of the sample using the organic matrix of CHCA according to the comparative example, the mass peak due to the CHCA occurs in a region of 400 m/z or less, and these mass peaks are not reproducible It is difficult to be removed as a noise signal. Therefore, in the case of the comparative example, it is predicted that it is difficult to distinguish the mass peak of the organic molecular compound and the noise signal from each other in the region where m/z is 500 or less, unlike the embodiment of the present invention. Conversely, according to the embodiment of the present invention, reliable mass spectrometry results can be obtained even in a region where m/z is 500 or less.

FIG. 4A to 4D are graphs showing mass spectrometry results of various organic molecular compounds using a sample plate including a photoreaction catalyst layer according to an embodiment of the present invention. The photoreaction catalyst layer has a $TiO_2$ nano scale structure.

Referring to FIG. 4A, the mass peak of a sample can be measured with $[M+K]^+$ and $[M+2K]^+$ in the case of arginine (molecular weight 174.2 Da), which is a low molecular substance as an organic molecular compound. Since the sample plate according to the embodiment of the present invention is manufactured by corroding with high concentration of KOH, a combination of the organic molecular compound and the K+ ion is obtained by K+ ions incorporated at this time.

Figure 4B:
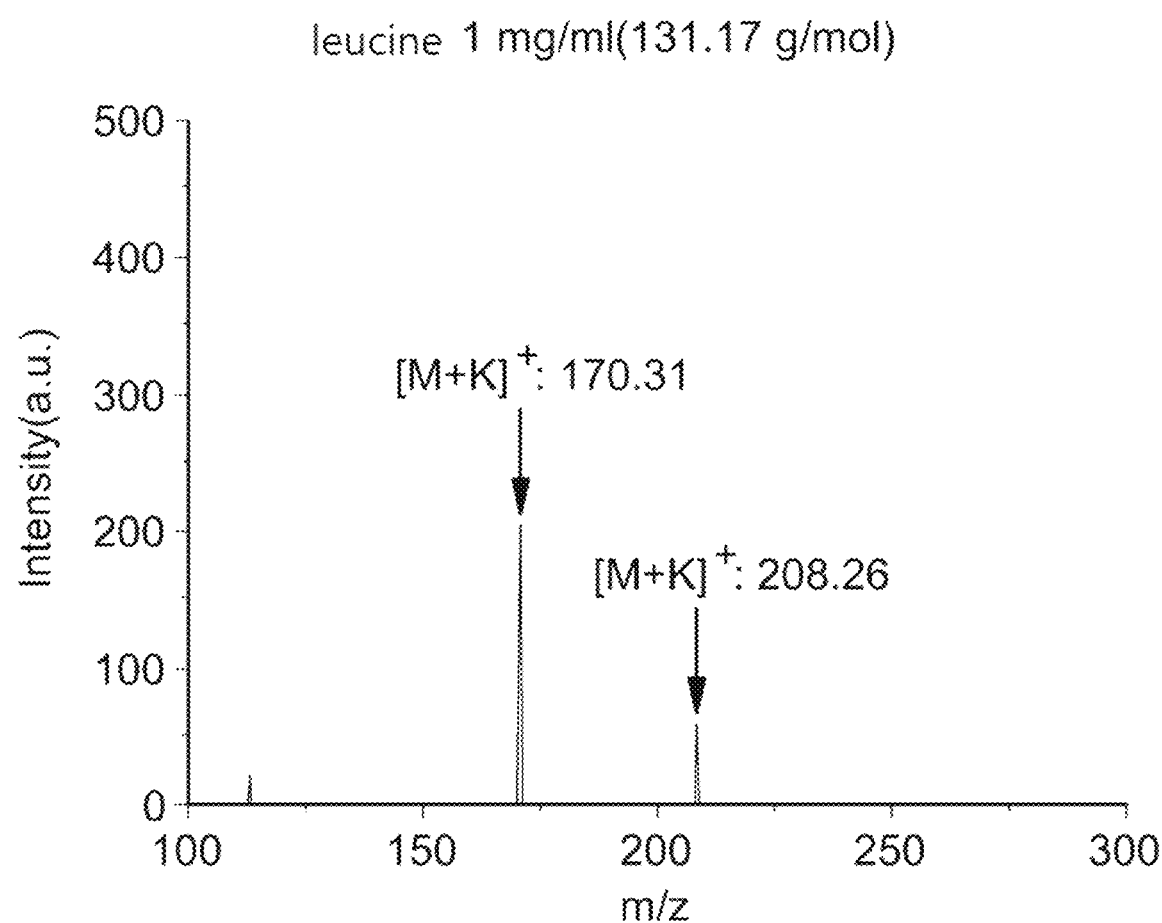

Referring to FIG. 4B, it can be seen that laser desorption/ionization mass spectrometry can be performed without a noise signal using a sample plate according to an embodiment of the present invention even in the case of another low-molecular substance, lucine (molecular weight 131.17 Da).

Figure 4C:
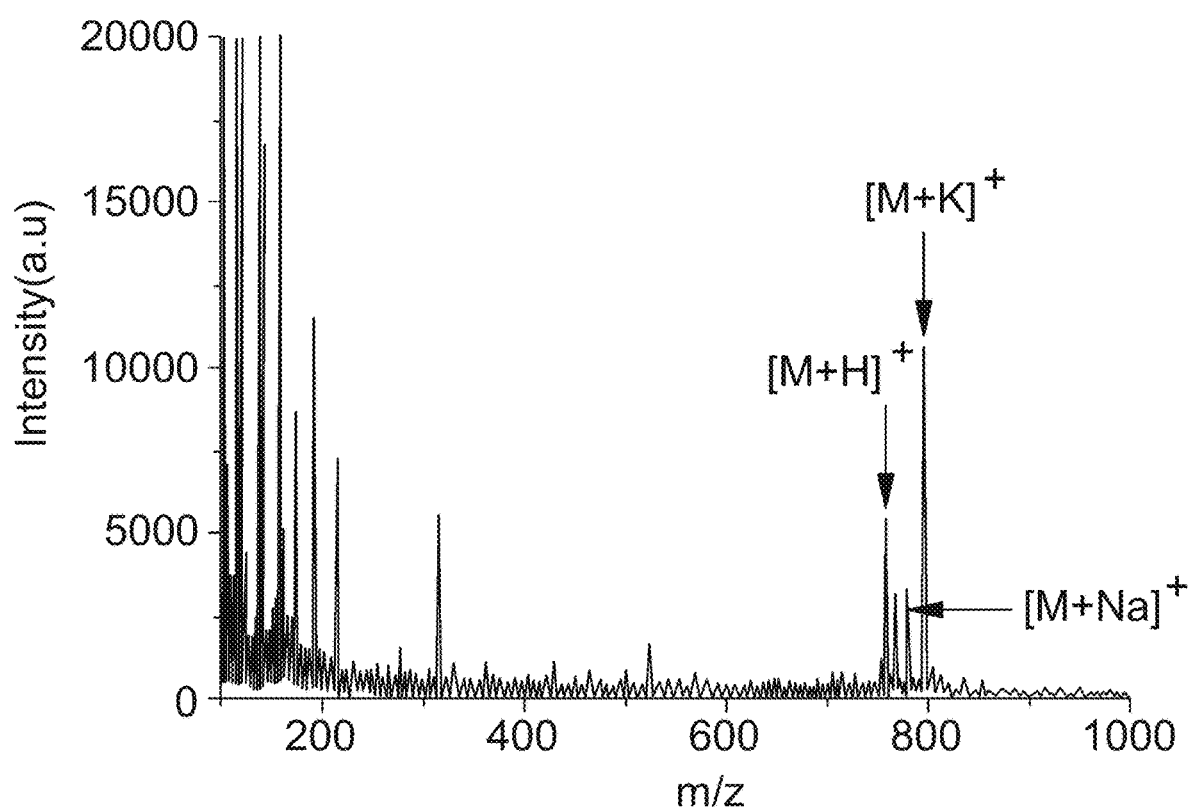

Referring to FIG. 4C, laser desorption/ionization mass spectrometry can also be performed using bradykinin (molecular weight 756.85 Da), which is a peptide composed of amino acid bonds as an organic molecular compound having a molecular weight of 500 Da or more, using a sample plate according to an embodiment of the present invention. Similarly, referring to FIG. 4D, laser desorption/ionization mass spectrometry can be performed using GHP9 (molecular weight 1007.18 Da) as an organic molecular compound having a molecular weight of 1,000 Da or more using a sample plate according to an embodiment of the present invention.

Figure 4D:
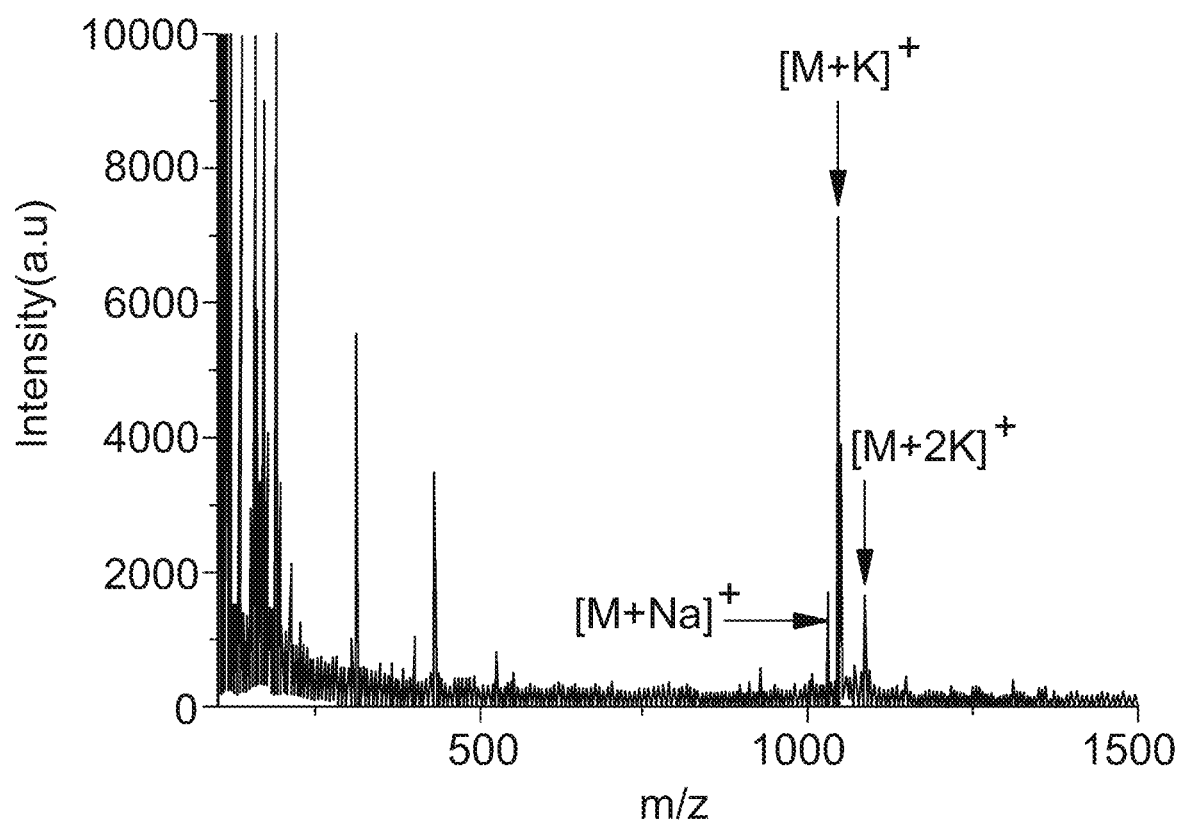

Referring FIG. 4D, even in case of GHP9 (molecular weight 1007.18 Da), which is a peptide composed of amino acid bonds as an organic molecular compound having a molecular weight of 1,000 Da or more, desorption/ionization mass spectrometry can be performed by a sample plate having a photoreactive catalyst layer according to an embodiment of the present invention.

The Tandem Mass analysis uses a method of generating and analyzing debris or fragments generated when colliding with an electron beam or a molecular beam. In the case of peptide compounds, peptide fragments may be formed by electron beam or molecular beam and comparative analysis can identify the amino acid sequence from the N-terminal to the C-terminal of the peptide compound. According to the embodiment of the present invention, instead of the electron beam or the molecular beam, the photocatalytic reaction of the sample to be analyzed on the photocatalytic catalyst layer may be induced only by irradiating ultraviolet light to the photocatalytic catalyst layer, Mass analysis based on Tandem mass analysis is possible. When the sample to be analyzed is a peptide, the sequence of the amino acid constituting the peptide can be determined by forming peptide fragments by the photolysis reaction and mass-analyzing the peptide fragments. Hereinafter, the tandem mass analysis using the sample plate according to the embodiment of the present invention will be described with reference to FIGS. 5A to 6C.

Figure 5A:
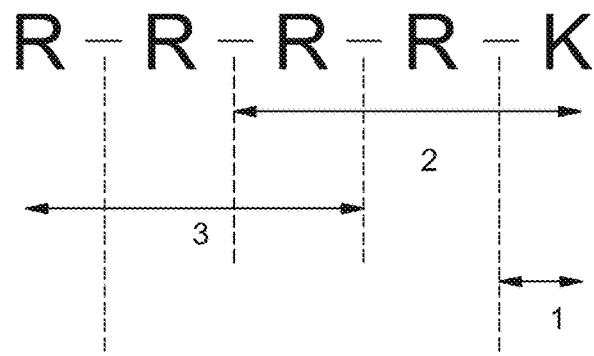
FIG. 5A shows primary sequence fragments according to the sequence of the R4K peptide, which is a sample to be analyzed for mass spectrometry.
Figure 5B:
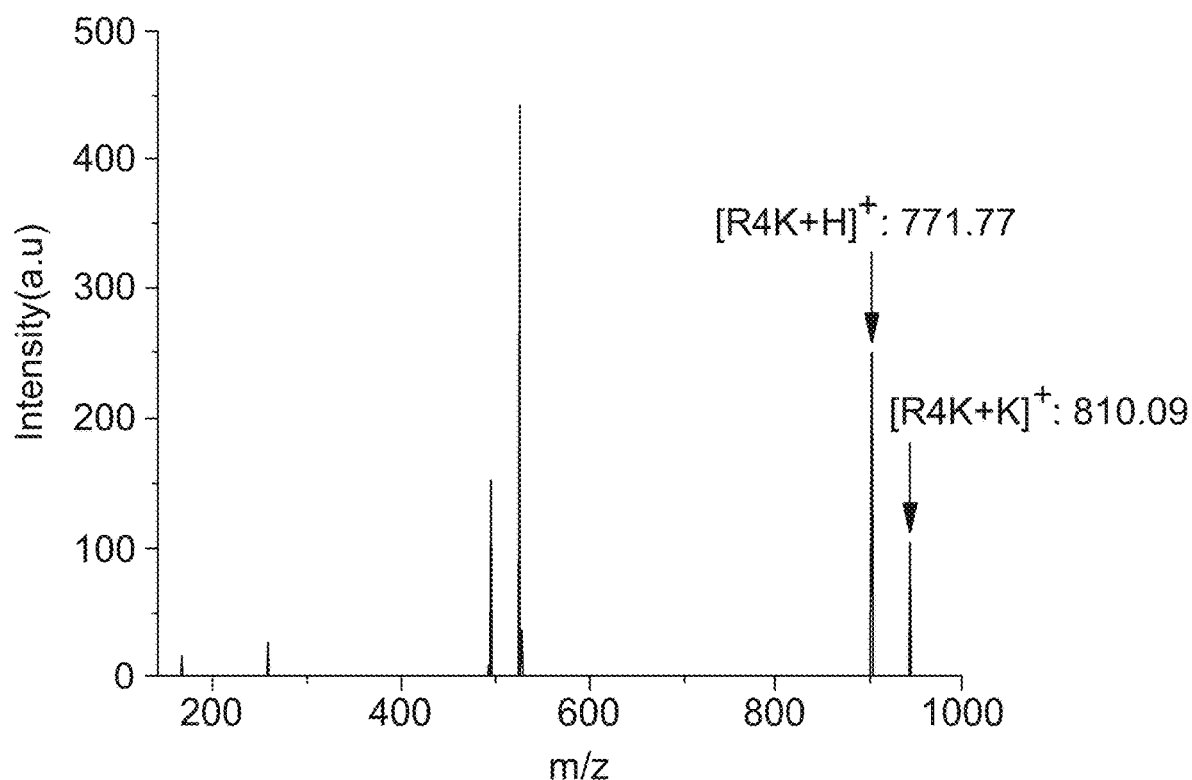
FIG. 5B and FIG. 5C are the graphs showing mass spectrometry results before and after irradiation with ultraviolet rays using a sample plate having photoreaction catalyst according to the embodiments of the present invention.
Figure 5C:
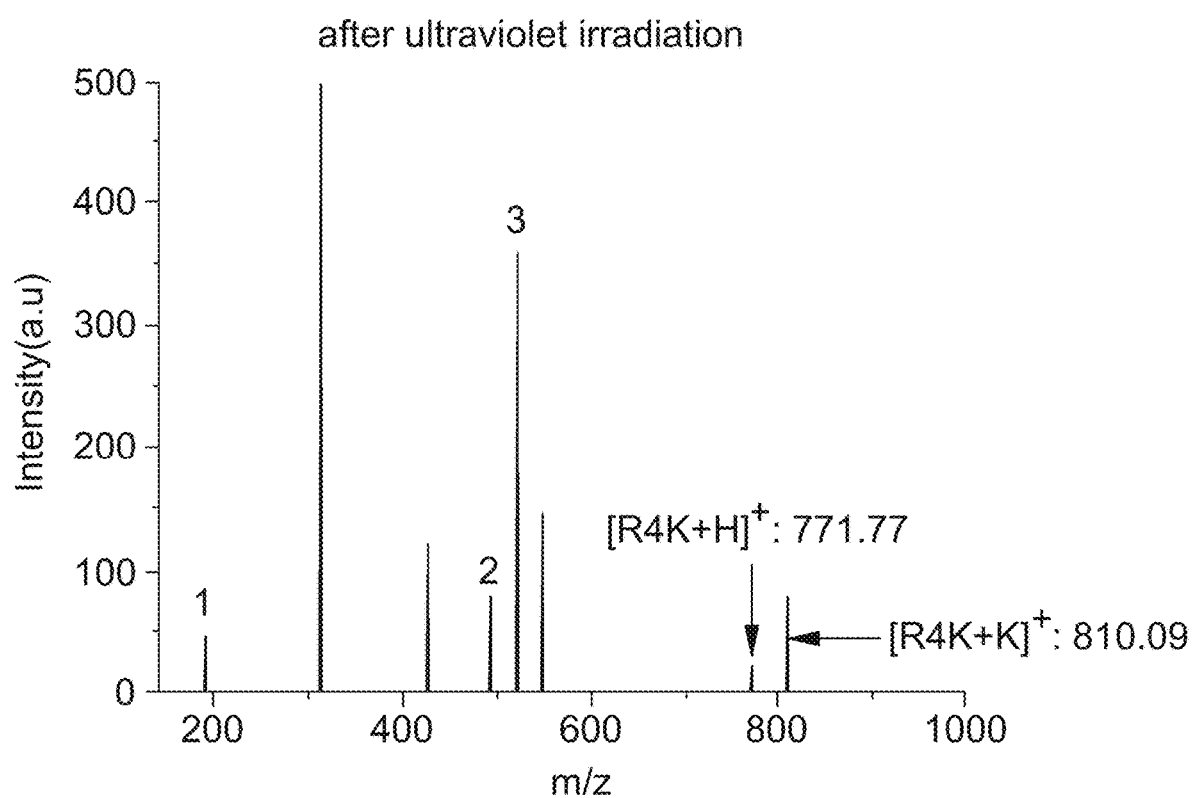

FIG. 5A shows primary sequence fragments according to the sequence of the R4K peptide, which is a sample to be analyzed for mass spectrometry. FIG. 5B and FIG. 5C are the graphs showing mass spectrometry results before and after irradiation with ultraviolet rays using a sample plate, respectively. The photoreactive catalyst layer according to an embodiment of the present invention is a $TiO_2$ layer having a porous nano scale structure. Laser desorption/ionization mass spectrometry is performed on these organic molecular compounds using Microflex Model of Bruker. The gain of a detector is 10× and the laser intensity is 90%.

Figure 6A:
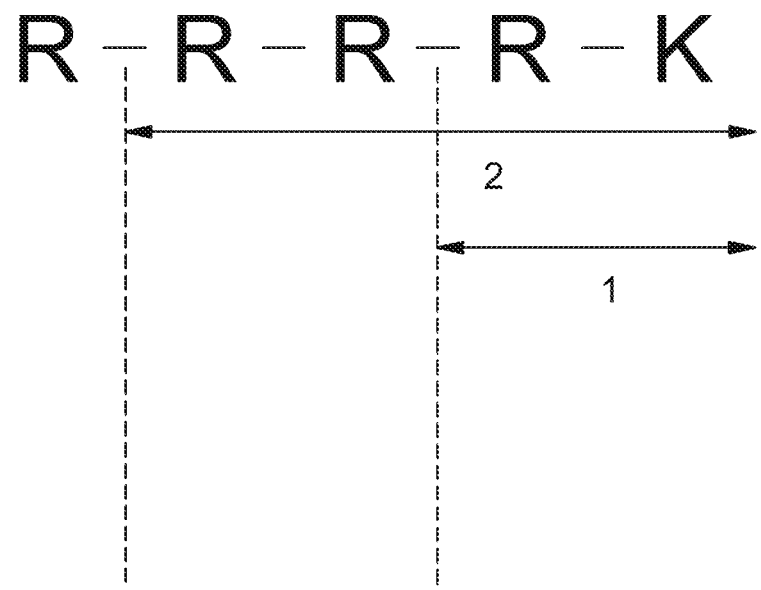
FIG. 6A shows primary sequence fragments according to the sequence of the R4K peptide, which is a sample to be analyzed for mass spectrometry according to a comparative example.

FIG. 6A shows primary sequence fragments according to the sequence of the R4K peptide, which is a sample to be analyzed for mass spectrometry according to a comparative example, and FIG. 6B and FIG. 6B are the graphs showing mass spectrometry results before and after ultraviolet irradiation. The mass spectrometry according to the comparative example was carried out using a Microflex model of Bruker. The detector had a gain of 12.6× and a laser intensity of 70%.

Referring to FIG. 5A, the sample to be analyzed for mass spectrometry is R4K peptide (1 mg/ml) with a molecular weight of 770.51 Da. The peptides may have three major fragments labeled as 1-3.

Referring to FIG. 5B, the mass peak of R4K is observed in the form of [M+K]+ and [M+Na]+ before UV irradiation for photodecomposition of the peptide. The results of mass spectrometry show that when the photolysis reaction is not carried out, fragmentation due to decomposition of the peptide does not occur only by laser irradiation for laser desorption/ionization mass spectrometry.

However, referring to FIG. 5C, it can be seen that after the ultraviolet (UV) irradiation, three peptide fragments whose sequences overlap each other are obtained. Thus, it can be seen that the tandem mass analysis capable of determining the sequence of the amino acids constituting the whole peptide can be performed from the total molecular weight of the peptide against the peptide before the photolysis reaction and the molecular weight of the three peptide fragments obtained after the photolysis reaction.

Referring to FIG. 6A, the sample to be analyzed for mass spectrometry is a R4K peptide (1 mg/ml) having a molecular weight of 770.51 Da, as described in FIG. 5a. Peptide fragments shown as 1 and 2 were detected through the above analysis.

Referring to FIG. 6B, the mass peak of R4K is observed in the form of [M+Na]+ prior to ultraviolet (UV) irradiation for photodecomposition of the peptide. The results of mass spectrometry show that when the photolysis reaction is not carried out, fragmentation due to decomposition of the peptide does not occur only by laser irradiation for laser desorption/ionization mass spectrometry.

Figure 6C:
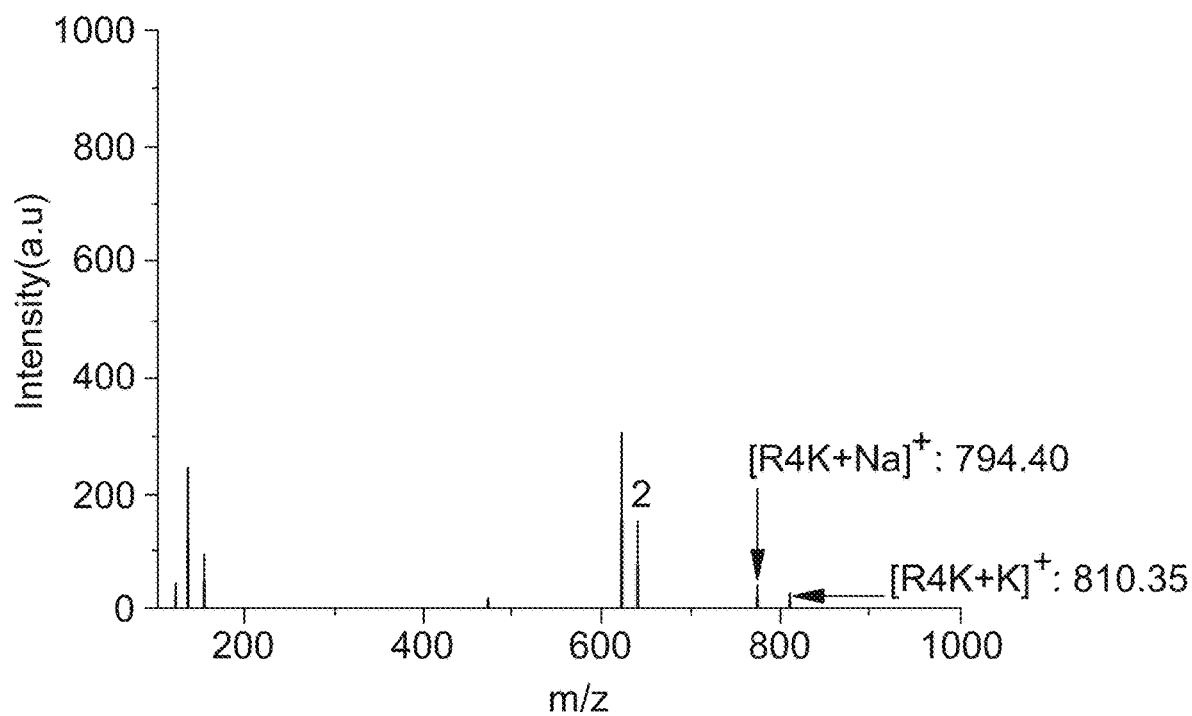

Referring to FIG. 6C, it can be seen that two peptide fragments are obtained after the ultraviolet (UV) irradiation. However, the information on the sequence is insufficient only by the total molecular weight of the peptide relative to the peptide before the photolysis reaction and the molecular weight of the two peptide fragments obtained after the photolysis reaction, so that the sequence analysis of the amino acids constituting the whole peptide cannot be easily performed.

According to the embodiments of the present invention, the result of the photolytic reaction can be varied due to the difference in the nano scale structure even if the same material and crystal structure are used, and the photoreactive catalyst layer according to the embodiment of the present invention has a sequence It is necessary to analyze tandem mass for analysis.

Figure 7A:
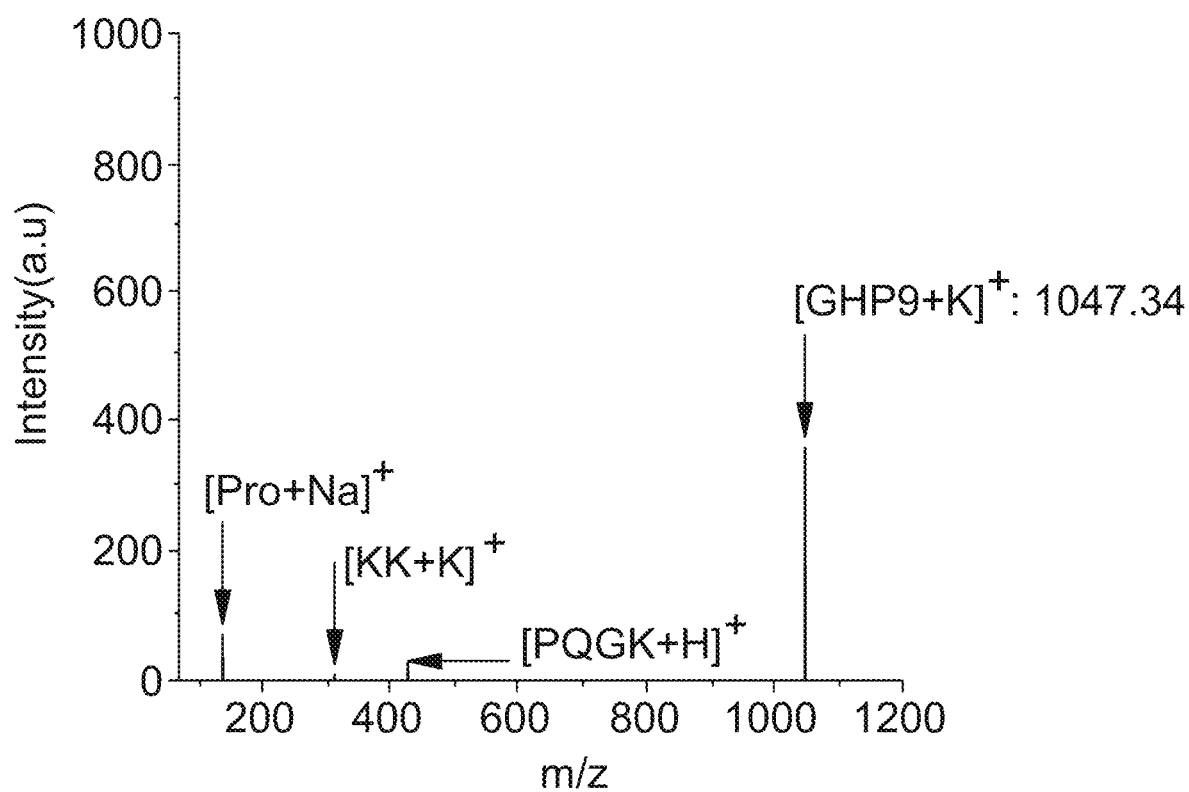
FIG. 7A and FIG. 7B are graphs showing mass spectrometry results of a GHP9 peptide before and after ultraviolet irradiation by using a sample plate according to an embodiment of the present invention.
Figure 7B:
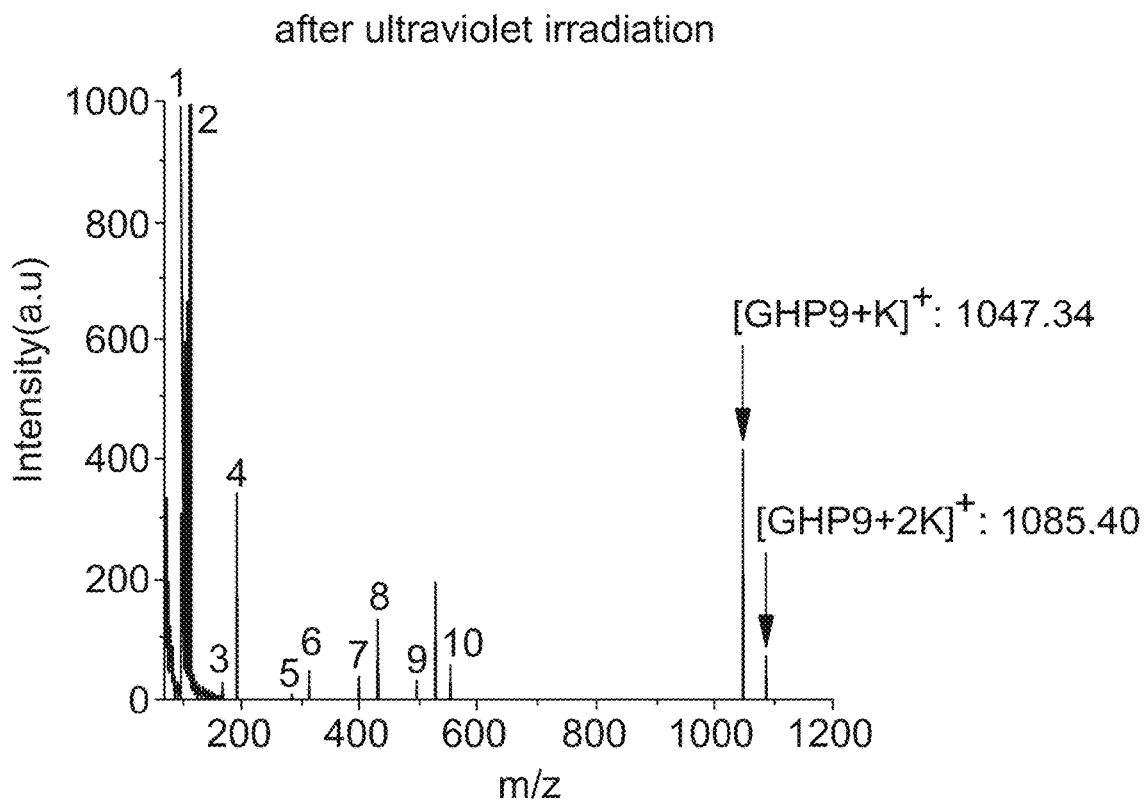

FIGS. 7A and 7B are graphs showing mass spectrometry results of a GHP9 peptide using ultraviolet irradiation and a sample plate having a photoreaction catalyst layer according to an embodiment of the present invention, the sequence of the amino acid obtained by mass spectrometry is shown. The photoreactive catalyst layer according to an embodiment of the present invention is a $TiO_2$ layer having a porous nano scale structure. Laser desorption/ionization mass spectrometry is performed on these organic molecular compounds using a Microflex model of Bruker. The gain of the detector is 10× and the laser intensity is 90%.

Referring to FIG. 7A, the sample to be analyzed for mass spectrometry is a GHP5 peptide (1 mg/ml) with a molecular weight of 1007.18 Da. Prior to photodecomposition using ultraviolet radiation, the mass peak of GHP9, an organic chemical sample, was observed in the form of [M+K]+.

Figure 7C:
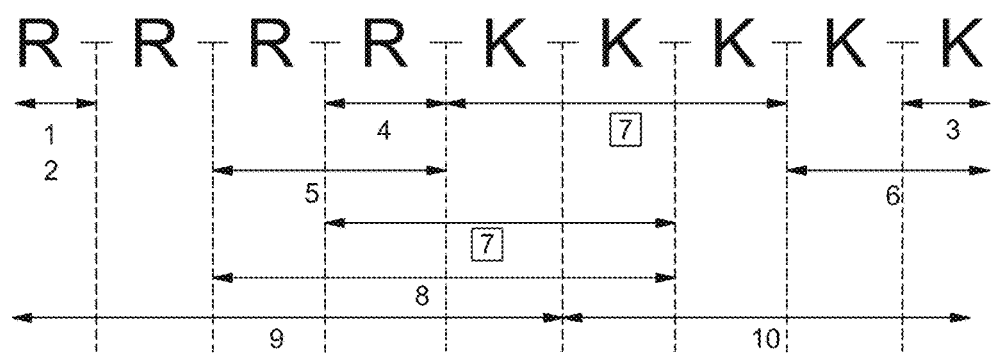
FIG. 7C shows an amino acid sequence obtained via mass spectrometry.

Referring to FIG. 7B, when the sample to be analyzed is fragmented through ultraviolet irradiation and subjected to mass analysis, mass peaks of ten peptide fragments whose sequences overlap with each other are detected. Using the total molecular weight of the peptide before the photolysis reaction and the molecular weight of the ten peptide fragments obtained after the photolysis reaction, it is possible to analyze the amino acid sequence of the GHP5 peptide as shown in FIG. 7C.

Figure 8A:
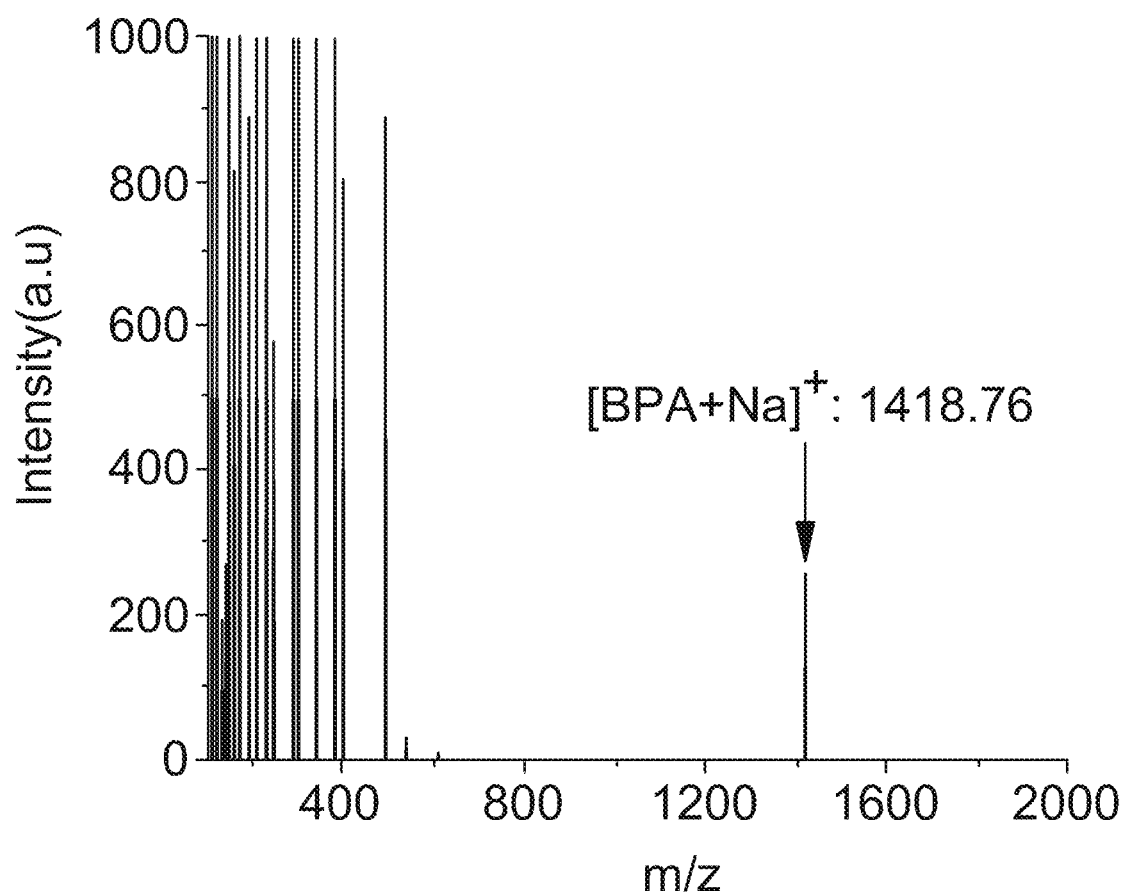
FIG. 8A and FIG. 8B are graphs showing mass spectrometry results of BPA peptides using a sample plate having a photoreaction catalyst layer according to an embodiment of the present invention before and after ultraviolet irradiation.
Figure 8B:
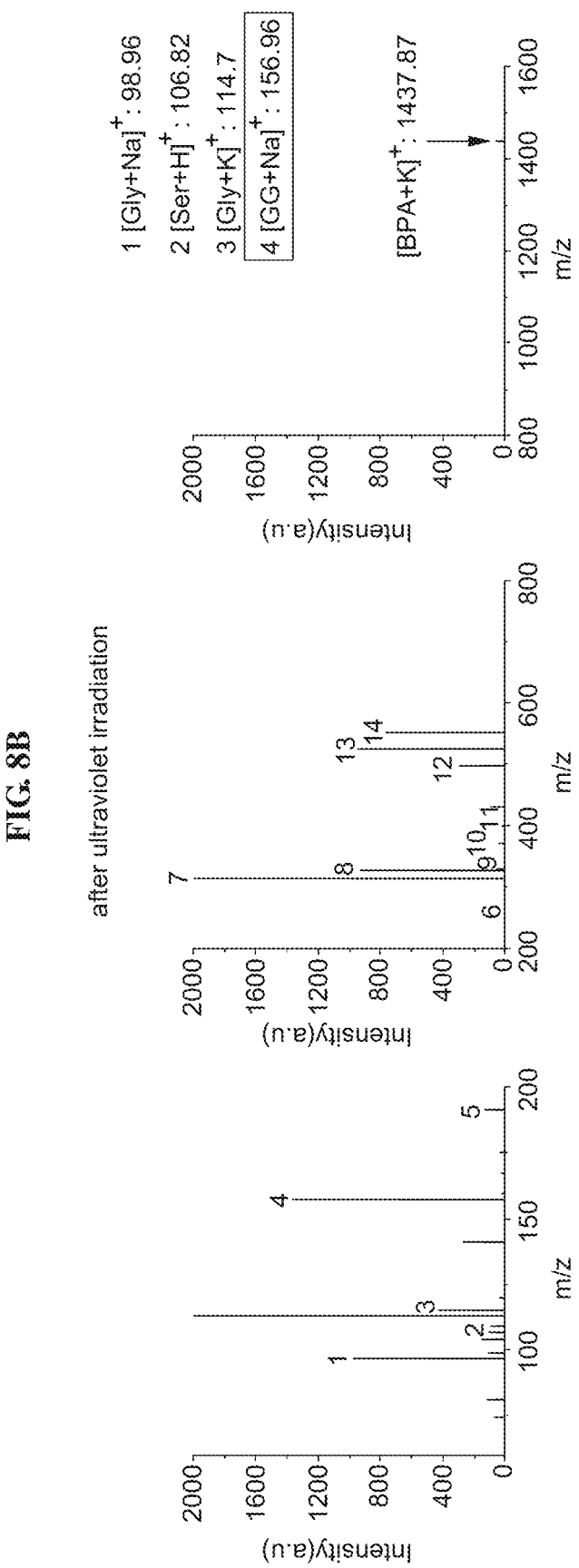
Figure 8C:
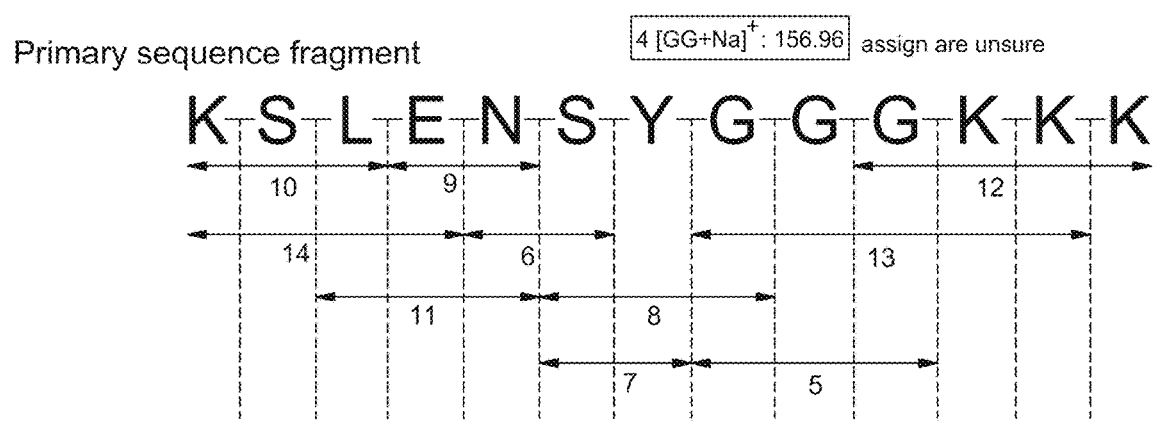
FIG. 8C shows a sequence of the amino acid obtained by mass spectrometry.

FIGS. 8A and 8B are graphs showing mass spectrometry results of BPA peptides using a sample plate having a photoreaction catalyst layer according to an embodiment of the present invention before and after ultraviolet irradiation. FIG. 8C shows the sequence of the amino acid obtained by mass spectrometry according to the embodiment of the present invention. The photoreactive catalyst layer is a TiO$_2$ layer having a porous nano scale structure. Using a Microflex model from Bruker, laser desorption/ionization mass spectrometry was performed on these organic molecular compounds, with a detector gain of 7× and a laser intensity of 70%.

Referring to FIG. 8A, the sample to be analyzed for mass spectrometry is a BPA peptide (1 mg/ml) having a molecular weight of 1395.56 Da. Prior to photodecomposition using ultraviolet irradiation, the mass peak of BPA, an organic chemical sample, was observed in the form of [M+K]+.

Referring to FIG. 8B, when the sample to be analyzed is fragmented through ultraviolet irradiation and subjected to mass analysis, mass peaks of 14 peptide fragments whose sequences overlap with each other are detected. Using the total molecular weight of the peptide before the photolysis reaction and the molecular weight of the 14 peptide fragments obtained after the photolysis reaction, it is possible to analyze the amino acid sequence of the BPA peptide as shown in FIG. 8C.

Figure 9A:
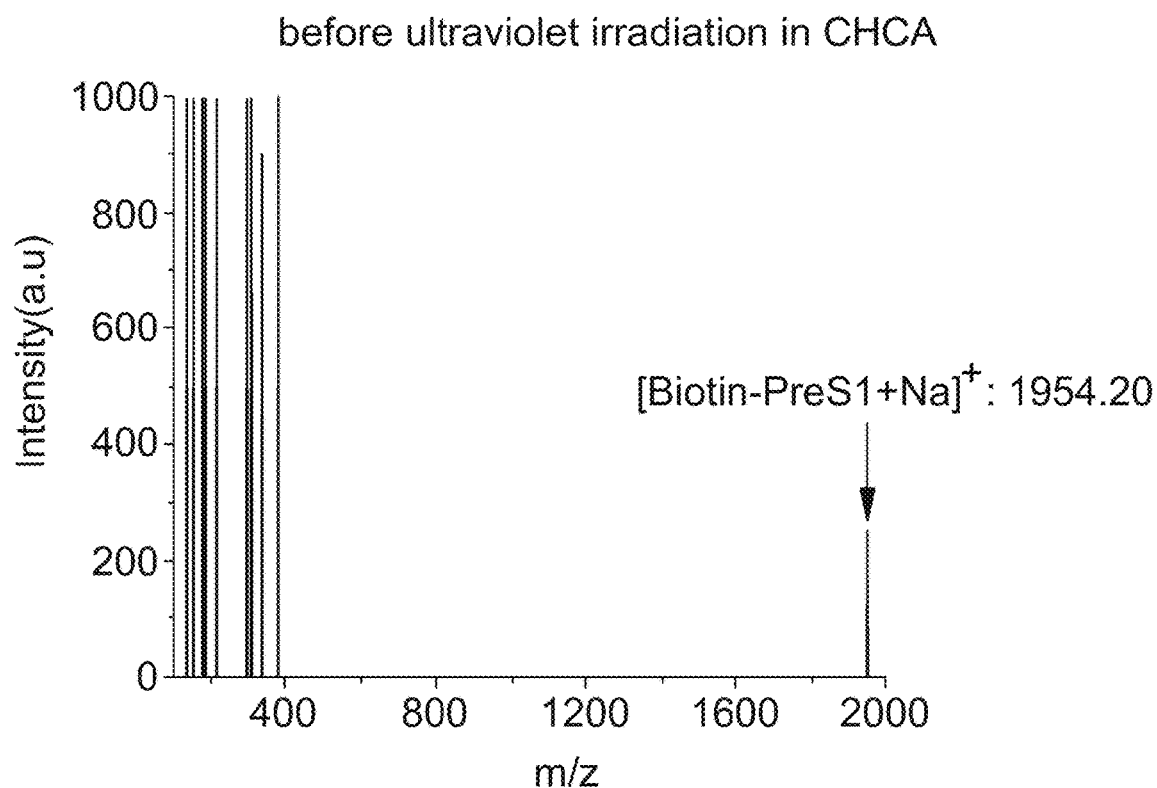
FIGS. 9A and 9B are graphs showing mass spectrometry results of a Biotin-PreS1 peptide using a sample plate having a photoreaction catalyst layer according to an embodiment of the present invention
Figure 9B:
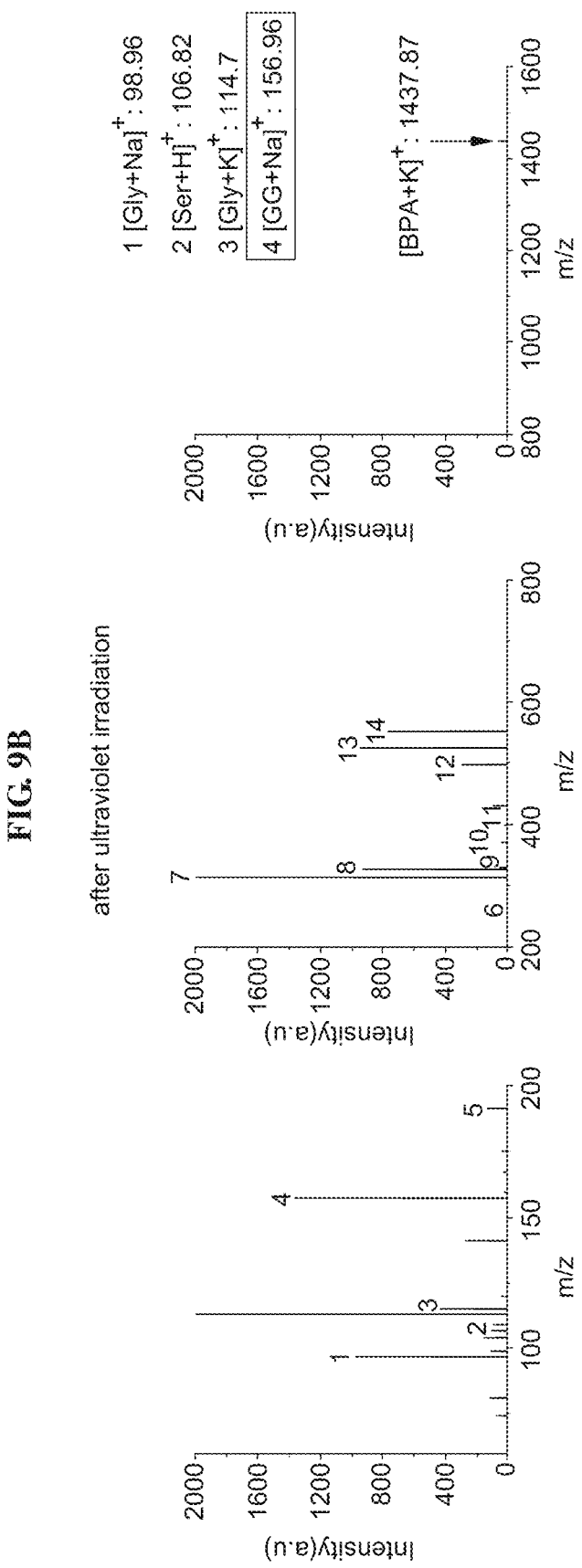

FIGS. 9A and 9B are graphs showing mass spectrometry results of a Biotin-PreS1 peptide before and after UV irradiation using a sample plate having a photoreaction catalyst layer according to an embodiment of the present invention. FIG. 8C shows the sequence of the amino acid obtained by mass spectrometry. The photoreactive catalyst layer is a TiO$_2$ layer having a porous nano scale structure. Using the Microflex model from Bruker, laser desorption/ionization mass spectrometry was performed on these organic molecular compounds. The detector has a gain of 8.6× and a laser intensity of 70%.

Referring to FIG. 9A, the sample to be analyzed for mass spectrometry is a PreS1 peptide (1 mg/ml) having a molecular weight of 1934.01 Da. Prior to photodecomposition by ultraviolet irradiation, the mass peak of PreS1, an organic chemical sample, was observed in the form of [M+K]+.

Figure 9C:
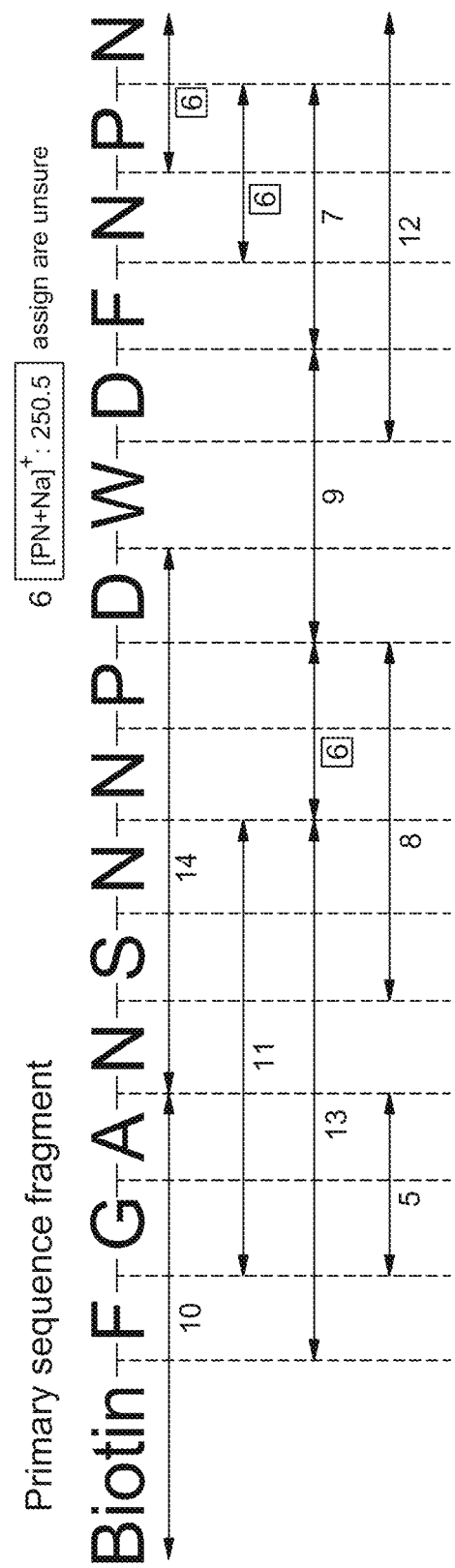
FIG. 9C shows the sequence of the amino acid obtained by mass spectrometry.

Referring to FIG. 9A, the sample to be analyzed is fragmented through ultraviolet irradiation, and subjected to mass analysis to detect mass peaks of 14 peptide fragments whose sequences overlap with each other. Analysis of the amino acid sequence possessed by a Biotin-PreS1 peptide such as that shown in FIG. 9C is possible by using the total molecular weight of the peptide compound before the photolysis reaction and the molecular weight of the abovementioned 14 peptide fragments obtained after the photolysis reaction.

In the case of a general MALDI-TOP mass spectrometry, when two or more kinds of ion samples having the same ionic mass (m/z) are mixed, it is impossible to identify the mixed ion sample because they are represented by the same mass peaks. However, When the sample is mixed, each ion forms a specific fragment. Therefore, it is possible to identify the mixed ions in the sample through analysis after formation of organic molecule fragments for the mixed sample.

According to an embodiment of the present invention, analysis of amino acid sequence can be performed on peptides having 3 to 15 amino acid residues via mass spectrometry by fragmenting organic molecules by ultraviolet rays using the photoreaction catalyst layer described with reference to FIGS. 5A to 9C.

Likewise, it is possible to apply the Tandem Mass Analysis method since photodecomposition reaction by irradiation of ultraviolet rays is induced without colliding with a conventional electron beam or molecular beam, and the organic molecule fragments generated through induction as above has the same characteristic. According to an embodiment of the present invention, identification of a mixed organic molecular compound can be possible.

According to an embodiment of the present invention, fragments of an organic molecular compound are formed through a photo-degradation reaction and analyzed to determine an organic molecular compound or an amino acid sequence of a peptide. In addition, an organic molecule fragment reflecting the structural specificity of an organic molecular compound such as an amino acid sequence can be obtained even for a sample having the same amount of ions in the photolysis reaction. The advantages of the present invention will be explained in more detail through the following disclosure.

Figure 10A:
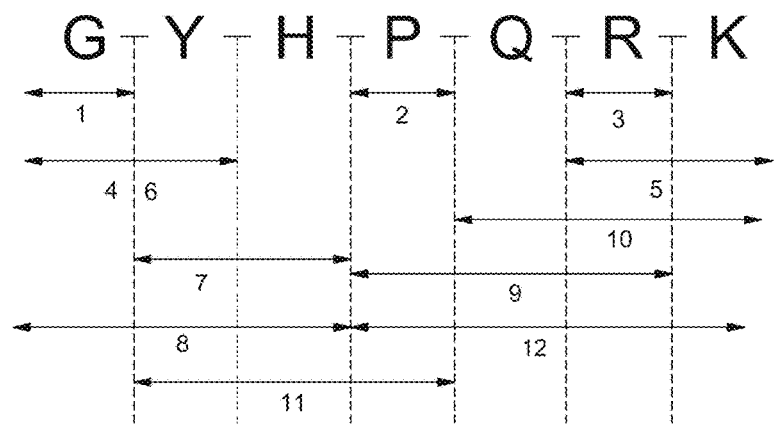
FIGS. 10A to 10C are graphs showing mass spectrometry results of organic molecular compounds having the same ionic mass using a photoreactive catalyst layer according to an embodiment of the present invention.
Figure 10A:
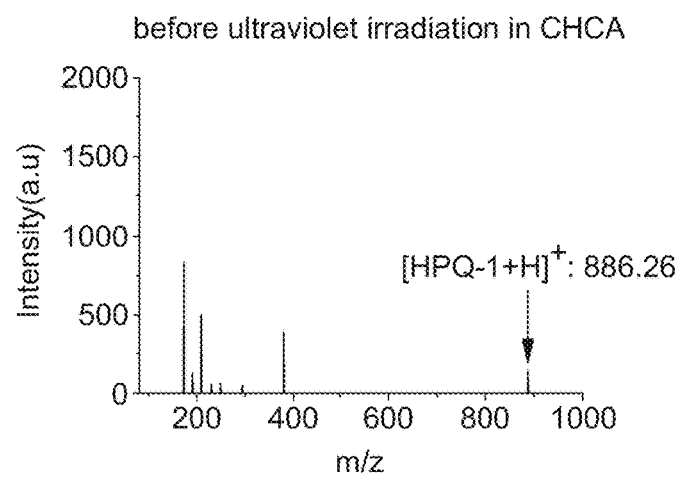
Figure 10A:
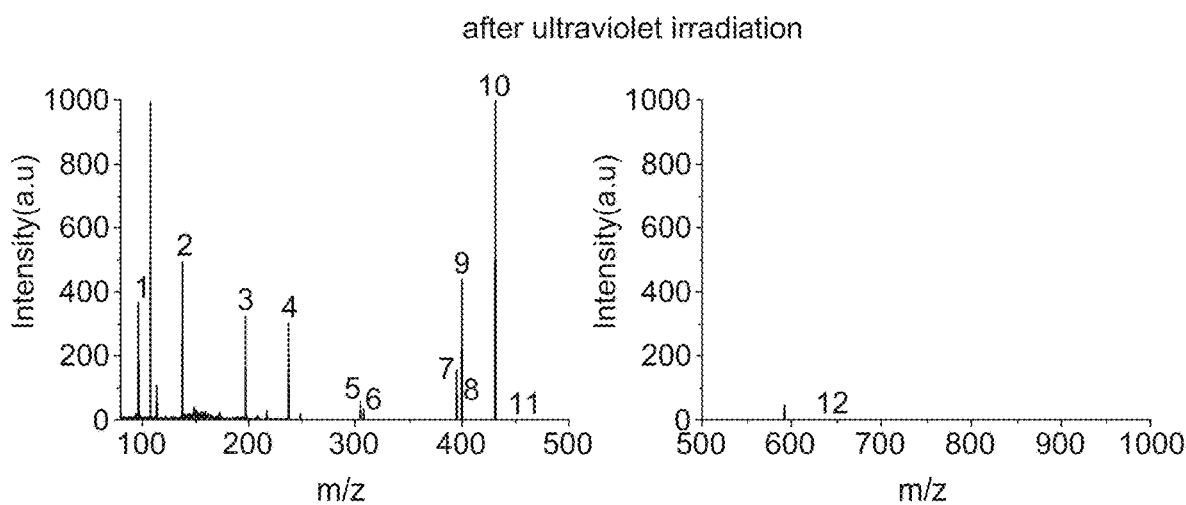
Figure 10B:
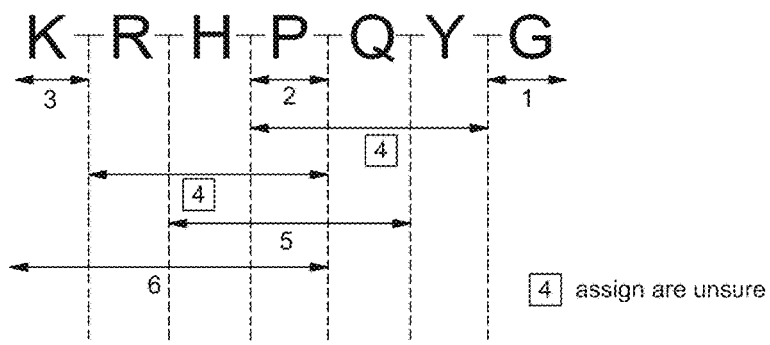
Figure 10B:
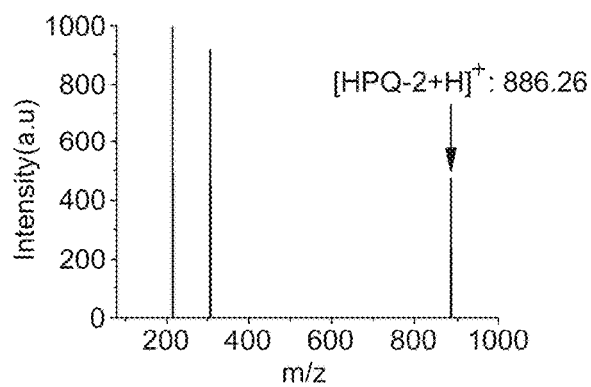
Figure 10B:
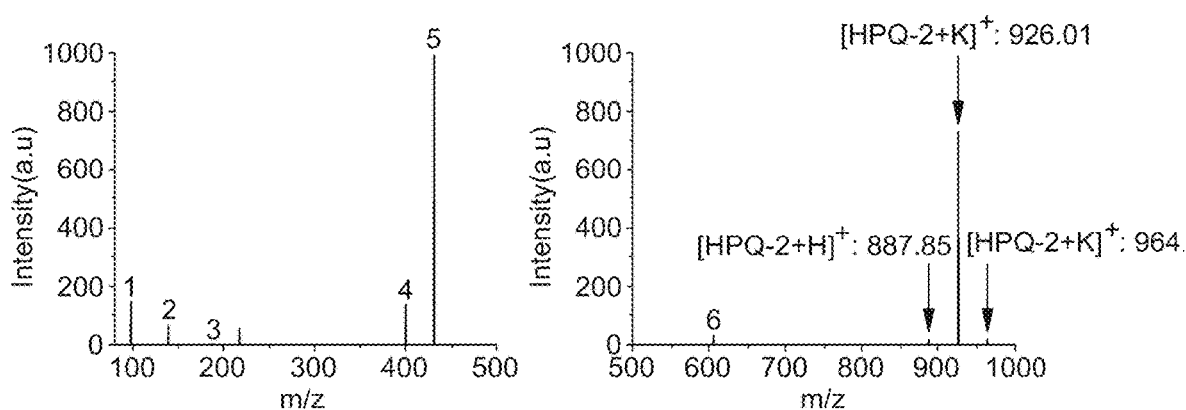
Figure 10C:
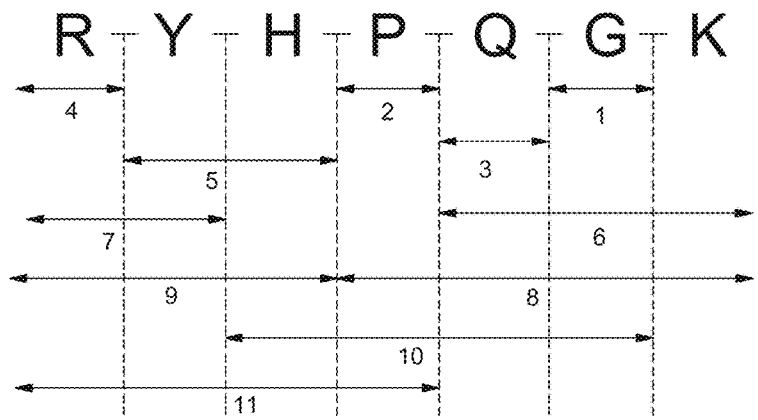
Figure 10C:
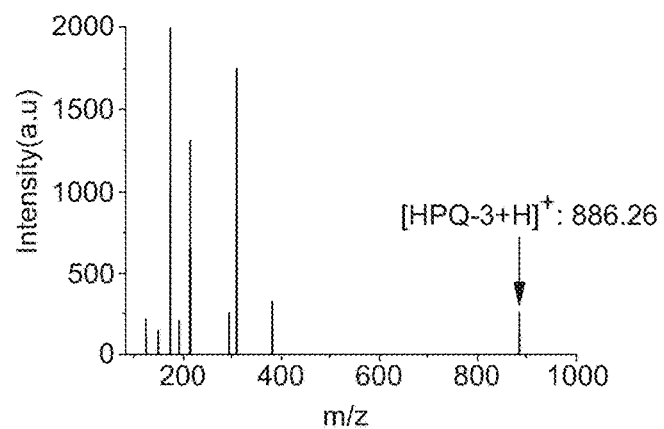
Figure 10C:
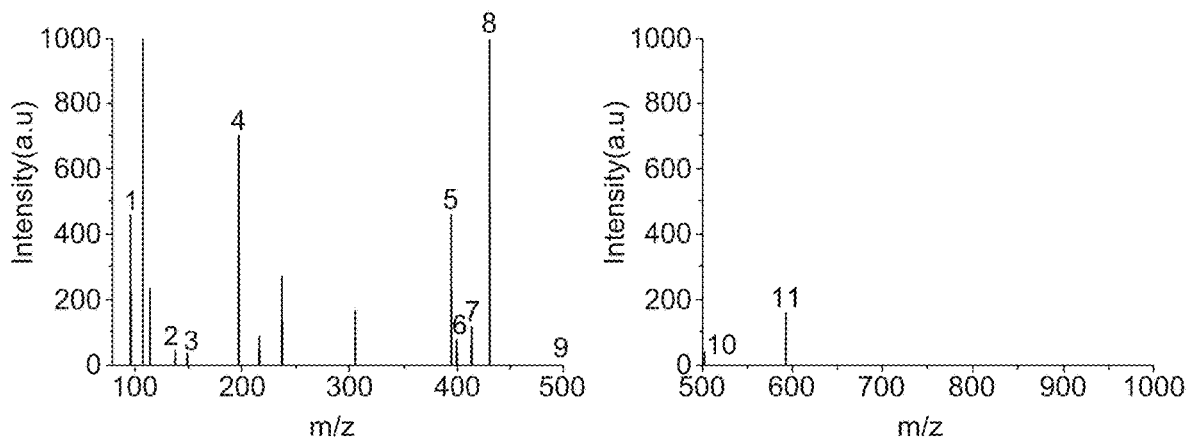

FIGS. 10A to 10C are graphs showing mass spectrometry results of organic molecular compounds having the same ionic mass using a photoreactive catalyst layer according to an embodiment of the present invention.

The organic molecular compounds shown in FIGS. 10A to 10C has a molecular weight of 884.46 Da and consisting of 7 amino acids. These compounds include HPQ-1 peptide having a sequence of GYHPQRK, HPQ-2 peptide having a sequence of KRHPQYG and HPQ-3 having a sequence of RYHPQGK. The photoreactive catalyst layer is a TiO$_2$ layer having a porous nano scale structure. Using a Microflex model from Bruker, laser desorption/ionization mass spectrometry was performed on these organic molecular compounds with a detector gain of 20× and a laser intensity of 90%.

Referring to FIG. 10A, the mass peak of the sample peptide HPQ-1 was observed in the form of [M+K]$^+$ before the photolysis reaction using UV. The mass spectrometric peaks after UV irradiation for the photolysis reaction of the sample peptides are obtained from twelve peptide fragments with overlapping sequences. Analysis of the amino acid sequence constituting the entire peptide was possible by analyzing the total molecular weight of the peptide before the photolysis reaction and the molecular weight analysis of the twelve peptide fragments obtained after photodegradation reaction.

Referring to FIG. 10C, before the photolysis reaction using UV, the mass peak of the sample peptide HPQ-2 was observed in the form of [M+K]$^+$. The mass spectrometric peak after the UV irradiation for the photolysis reaction of the sample peptide is obtained from six peptide fragments which are sequence-unlike HPQ-1. Analysis of the amino acid sequence constituting the whole peptide was possible by analyzing the total molecular weight of the peptide before the photolysis reaction and the molecular weight analysis of the six peptide fragments obtained after the photolysis reaction.

Referring to FIG. 10C, the mass peak of the sample peptide HPQ-3 was observed in the form of [M+K]$^+$ before the UV degradation reaction. In the case of the mass spectrometric peak after UV irradiation for the photodecomposition reaction of the sample peptides, 11 peptide fragments having sequences overlapping with HPQ-1 and HPQ-2, which are the peptides previously analyzed, are obtained as shown in the drawings. Analysis of the amino acid sequence constituting the entire peptide was possible by analyzing the total molecular weight of the peptide before the photolysis reaction and the molecular weight analysis of the eleven peptide fragments obtained after the photolysis reaction.

Figure 11A:
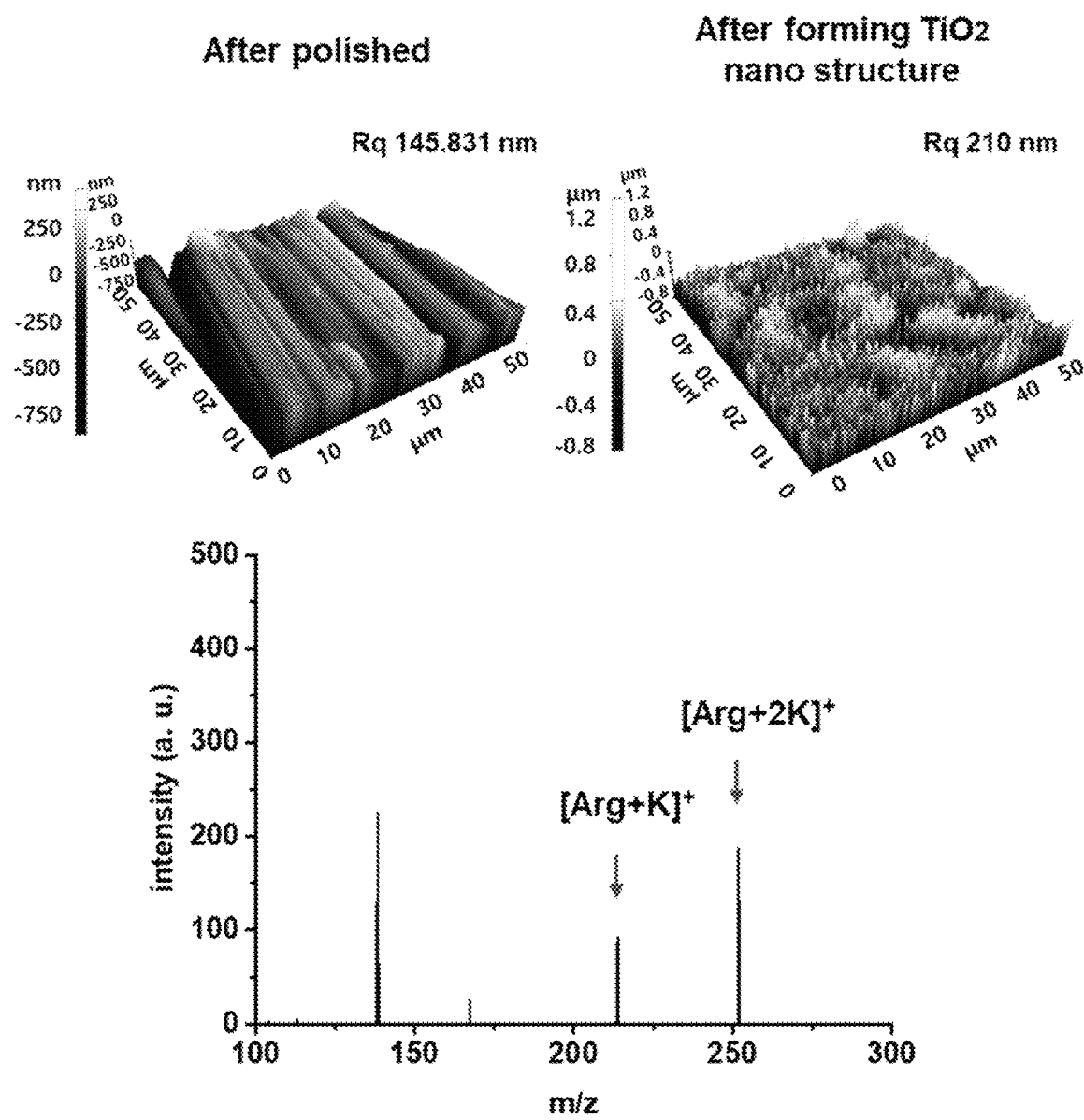
FIGS. 11A and 11B illustrate atomic spectroscope images of substrates having surfaces of a uni-directional stripe pattern and bi-directional stripe pattern before polished and after forming $TiO_2$ nano-structure, respectively
Figure 11B:
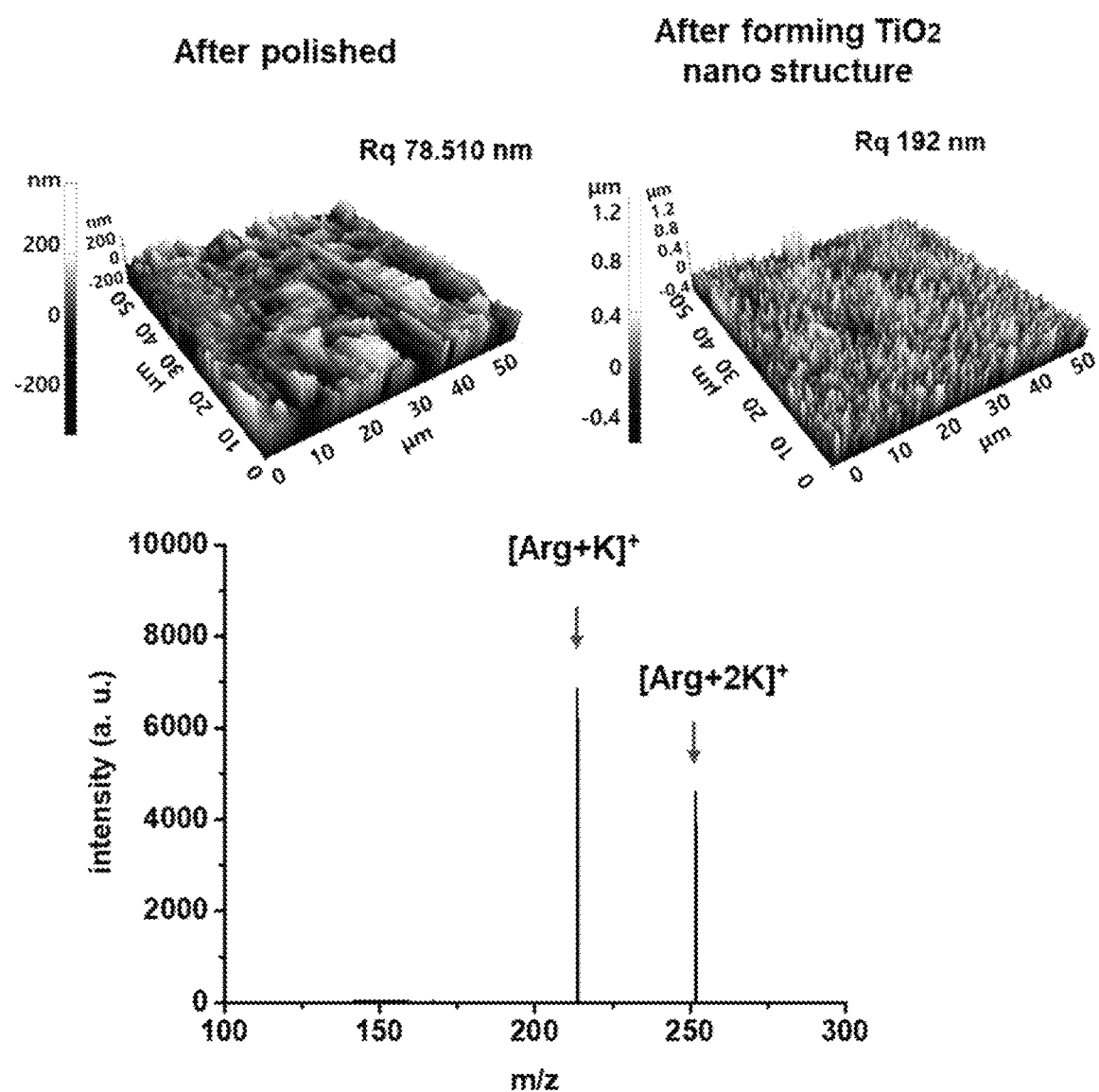

FIGS. 11A and 11B illustrate atomic spectroscope images of substrates having surfaces of a uni-directional stripe pattern and bi-directional stripe pattern before polished and after forming $TiO_2$ nano-structure, respectively. Diamond sand having 500 mesh was used for polishing the substrate.

Referring FIGS. 11A and 11B, the polished surface of the substrates may be differentiated from each other depending on the uni-directional stripe pattern and bi-directional stripe pattern.

As showed in FIG. 11A, a bare sample plate having a photocatalytic catalyst layer of $TiO_2$ according to an embodiment of the present invention does not generate a mass peak when there is no sample to be analyzed. Particularly, it should be noted that there is no mass peak in the region of 500 m/z or less. Unlike this fact, referring to FIG. 11B, in the case of the sample using the organic matrix of CHCA according to the comparative example, the mass peak due to the CHCA occurs in a region of 400 m/z or less, and these mass peaks are not reproducible. Thus, it is difficult to be removed as a noise signal. Therefore, in the case of the comparative example, it is predicted that it is difficult to distinguish the mass peak of the organic molecular compound and the noise signal from each other in the region where m/z is 500 or less, unlike the embodiment of the present invention. Conversely, according to the embodiment of the present invention, reliable mass spectrometry results can be obtained even in a region where m/z is 500 or less.

When analyzing arginine (molecular weight 174.2 Da) of the same concentration using this polished substrate, the mass peak of the sample with $[M+K]^+$ and $[M+2K]^+$ can be measured without a noise occurring in the low range of m/z. In addition, when the substrates are polished in one direction of the stripe pattern or in both directions of the crossing pattern, it was seen that the level of the mass peaks are greatly different according to the patterns. In the case of a bi-directional polished substrate having a crossing stripe pattern, it can be seen that the ionization of the analyte occurs more effectively than that of substrate having uni-direction stripe pattern.

Figure 12A:
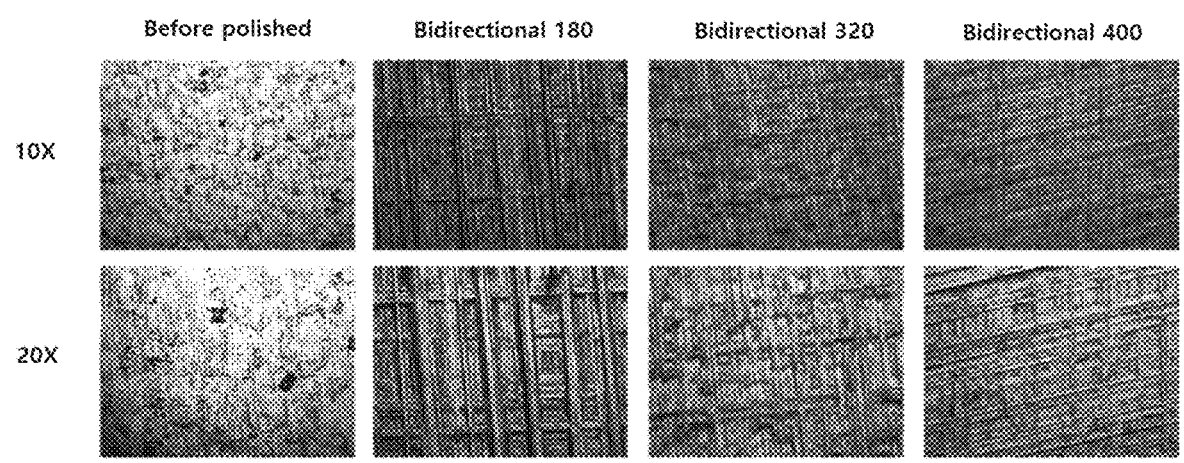
FIG. 12A is optical images of substrates in which the surface of the substrates SS which are not yet exposed to corrode the surface of the substrate SS and the substrates SS are subjected to be polished by diamond sand paper having roughness 180, 320, 400 and 500 mesh.

FIG. 12A is optical images of substrates SS in which the surface of the substrates SS which are not yet exposed to corrode the surface of the substrate SS and the substrates SS are subjected to be polished by diamond sand paper having roughness 180, 320, 400 and 500 mesh. The optical images are at a magnification of 10 and 20. As shown in the optical microscope images, the bi-directional stripe pattern can be observed. Also, when the sand papers having roughnesses of 180, 320, and 400 mesh are utilized, as the roughness of the sand paper becomes smaller, the interval of the adjacent stripes are denser and the depth of the stripes are shallower.

Figure 12B:
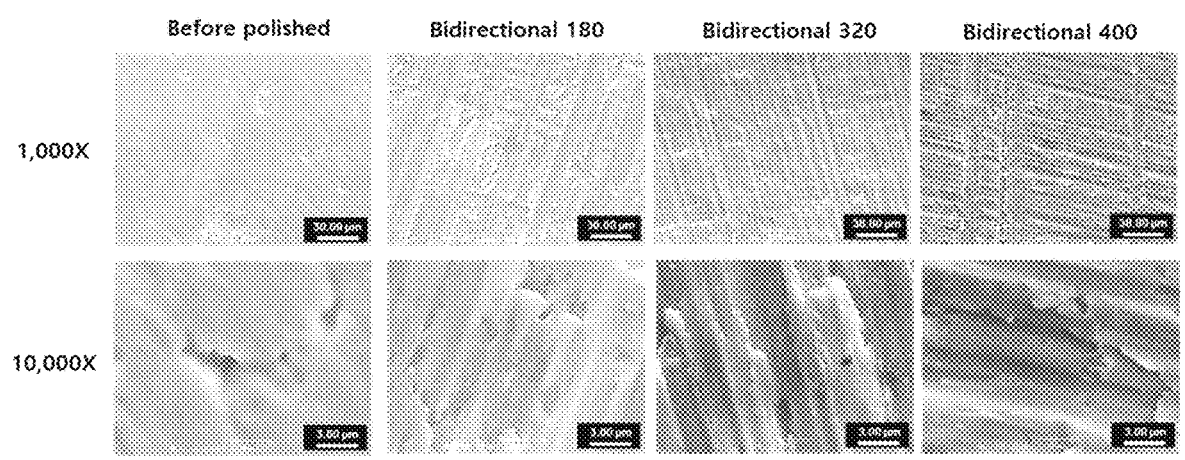
FIG. 12B illustrates scanning electron microscope images of the surface of the substrates which are polished to form the bi-direction stripe pattern by using diamond sand paper having roughness of 180, 320 and 400 mesh, respectively.

FIG. 12B illustrates scanning electron microscope images of the surface of the substrates SS which are polished to form the bi-direction stripe pattern by using diamond sand paper having roughness of 180, 320 and 400 mesh, respectively. The surface of the substrate was observed using the scanning electron microscope at a magnification of 1,000 and 10,000. As shown in 12B, bi-directional stripe pattern can be observed by comparing the surface of the polished substrate with bare substrate. The surface of the unpolished substrate has a roughness similar as that of the substrate polished by the sand paper with roughness of 320 mesh, but no surface structure related with the direction of the surface polishing was observed. When the sand paper having a roughness of 180, 320, and 400 mesh is used, as the roughness of the sand paper becomes smaller, the interval of the adjacent stripes is denser and the depth of the stripes are shallower.

Figures 13A, 13B:
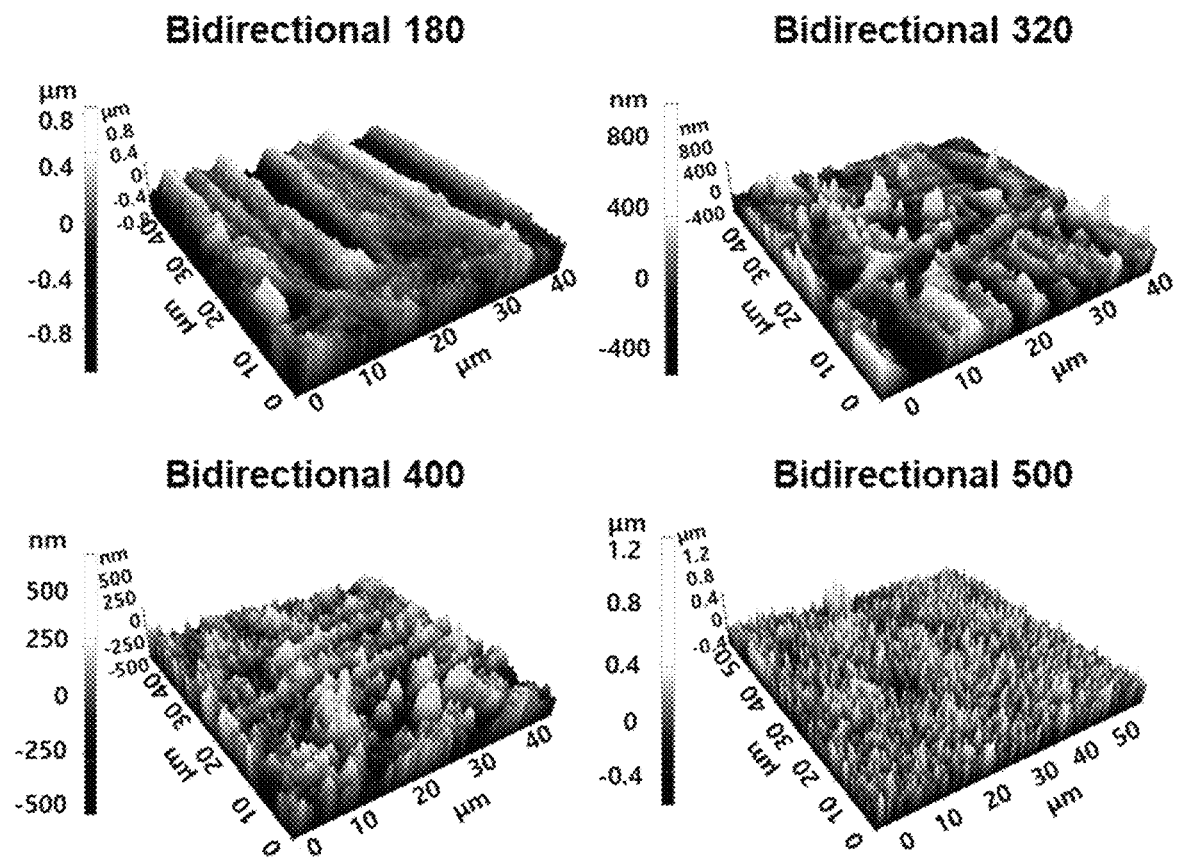
FIG. 13A shows surface roughness observed by atomic force microscope on the surface of the substrates which is polished by using the diamond sandpaper having the roughness of 180, 320 and 400 mesh to form the bi-directional stripe pattern and then is corroded.
FIG. 13B shows the surface roughness observed by atomic force microscope on the substrate SS on which the nano scale structure (i.e., nano-wires) are formed by using the diamond sand paper having roughness 180, 320, 400 and 500 mesh, respectively.

FIG. 13A shows surface roughness observed by atomic force microscope on the surface of the substrates SS which is polished by using the diamond sandpaper having the roughness of 180, 320 and 400 mesh to form the bi-directional stripe pattern and then is corroded. As shown in the atomic force microscope image, bi-directional stripe pattern can be observed by comparing the surface of the polished substrate having the nano scale structure with bare substrate having the nano scale structure. When the sand paper having a roughness of 180, 320, and 400 mesh is used, as the roughness of the sand paper becomes smaller, the interval of the adjacent stripes is denser and the depth of the stripes are shallower.

FIG. 13B shows the surface roughness observed by atomic force microscope on the substrate SS on which the nano scale structure (i.e., nano-wires) are formed by using the diamond sand paper having roughness 180, 320, 400 and 500 mesh, respectively. The results are compared with each other. The degree of roughness was calculated using the Rq value, which are shown in FIG. 13B.

The results show that the area of the substrate surface can be adjusted by polishing the diamond sand with different roughness as shown in FIGS. 12A and 12B. Also, the results of FIG. 13B show that the roughness of the surfaces is generally similar to each other regardless of the roughness of the diamond sand paper used for the polishing process. Since the degree of ionization is determined according to the area of the nano scale structure interfaced with the analyte, the area of the nano scale structure produced according to the roughness of the nanowire may be determined by the pre-processing including the polishing process before forming the nano scale structure.

Figure 14A:
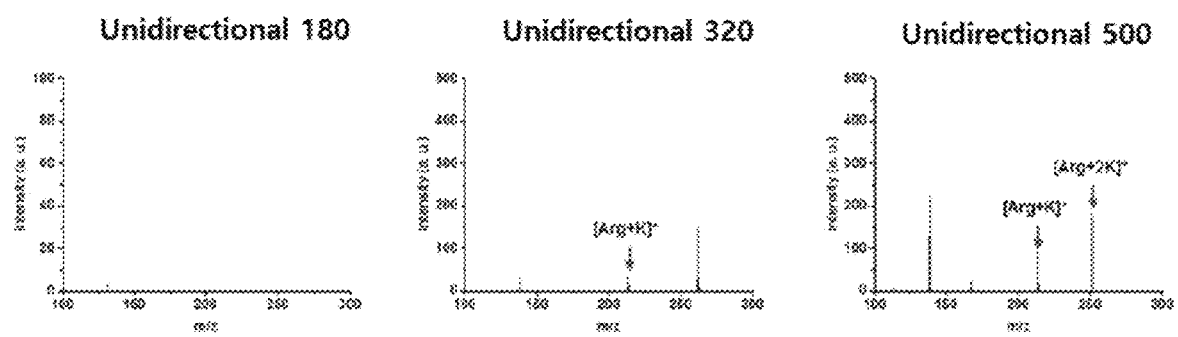
FIG. 14A shows results of mass spectroscopy analysis for various organic molecule compound by using the sample plate having photo reactive catalysis layer fabricated according to the present invention.

FIG. 14A shows results of mass spectroscopy analysis for various organic molecule compound by using the sample plate having photo reactive catalysis layer fabricated according to the present invention. The photo reactive catalysis layer has $TiO_2$ nano scale structure.

Referring to FIG. 14A, in the case of arginine (molecular weight 174.2 Da) as an organic molecular compound, the mass peak of a sample can be measured with $[M+K]^+$ and $[M+2K]^+$. Since the sample plate is fabricated by corroding with high concentration of KOH, a combination of the organic molecular compound and the $K^+$ ion is obtained. Also, it can be seen that the laser desorption/ionization mass spectrometry can be performed without a noise signal using the sample plate according to the embodiment of the present invention.

Figure 14B:
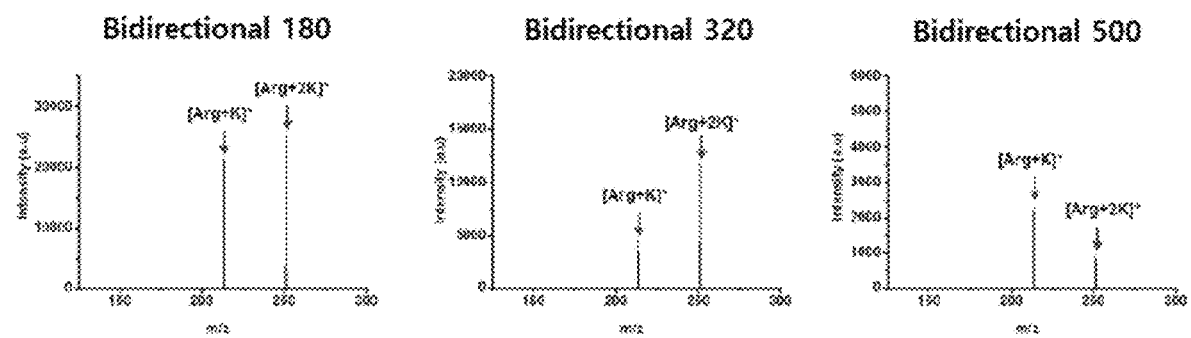
FIG. 14B shows the results of mass spectrometry analysis when the substrate is polished by using diamond sand paper of roughness 180, 320, and 400 mesh to form uni-directional stripe pattern and bi-directional stripe pattern.

FIG. 14B show the results of mass spectrometry analysis when the substrate is polished by using diamond sand paper of roughness of 180, 320, and 400 mesh to form uni-directional stripe pattern and bi-directional stripe pattern. The analyte is arginine (molecular weight 174.2 Da), which is a low-molecular substance.

As shown in FIG. 14A, in the case of the uni-directional stripe pattern formed by diamond sand paper having a roughness of 180, the mass analysis peak was not observed. This result shows that the area of nano-structure is not sufficient to generate the ions required for mass peak generation. A mass spectrometric peak was found in the substrates polished by a diamond sand paper having roughness of 320 and 500. This is because the ionization efficiency per unit area was increased due to the increase of substrate surface area for forming nano scale structure with increasing surface roughness.

As shown in FIG. 14B, in the case of the bi-directional stripe pattern formed by using the diamond sandpaper having a roughness of 180 mesh, the mass analysis peak was also observed in the sample after fabricating the nano scale structure. In the case of a substrate having a bi-direction stripe pattern, the mass peaks were markedly higher than those of a substrate having an uni-direction stripe pattern. This result shows that the substrate surface area for forming the nano-structure may be increased due to the increase of the roughness of the substrate surface due to the bi-directional polishing, and the ionization efficiency per unit area may be improved so that ionization necessary for mass peak generation may be enhanced.

According to an embodiment of the present invention, sequence analysis can be performed on peptides having 3 to 15 amino acid residues via mass spectrometry by fragmenting organic molecules by ultraviolet rays using the photoreaction catalyst layer described with reference to FIGS. 5A to 14B.

Likewise, it is possible to apply the Tandem Mass Analysis method since photodecomposition reaction by irradiation of ultraviolet rays is induced without colliding with a conventional electron beam or molecular beam, and the organic molecule fragments generated through induction as above has the same characteristic. According to an embodiment of the present invention, identification of a mixed organic molecular compound can be possible.

According to an embodiment of the present invention, fragments of an organic molecular compound are formed through a photo-degradation reaction and analyzed to determine an organic molecular compound or an amino acid sequence of a peptide. In addition, an organic molecule fragment reflecting the structural specificity of an organic molecular compound such as an amino acid sequence can be obtained even for a sample having the same amount of ions in the photolysis reaction. The advantages of the present invention will be explained in more detail through the following disclosure.

According to the embodiments of the present invention, when the peptide fragment produced by the light irradiation and the decomposition reaction are subjected to mass spectrometry using a laser desorption/ionization method. A fragment of a peptide reflecting the structural specificity according to the amino acid sequence can be obtained, and the amino acid sequence constituting the peptide can be analyzed using the molecular weight of the peptide fragments. While the foregoing embodiments are directed to peptides, embodiments of the present invention are not limited to these peptides, it is to be understood that the present invention can be applied for identifying the organic analytical samples with distinct specific binding that may undergo different decomposition reactions by light irradiation, as well as other peptides.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A sample plate for laser desorption/ionization mass spectrometry comprising,
    a substrate comprising a photoreaction catalyst layer on a surface of the substrate, the photoreaction catalyst layer comprising a metal oxide of the same metal as the substrate,
    wherein the photoreaction catalyst layer is formed by corrosion of a metal on the surface of the substrate creating the metal oxide,
    wherein a sample to be analyzed is disposed on the photoreaction catalyst layer.

2. The sample plate of claim 1, wherein the metal oxide comprises an oxide layer on a surface of the substrate.

3. The sample plate of claim 1, wherein the metal oxide comprises a metal oxide of at least one of titanium (Ti), tantalum (Ta), tin (Sn), tungsten (W), zinc (Zn), vanadium (V), ruthenium (Ru), iridium (Ir) and iron (Fe).

4. The sample plate of claim 1, wherein the metal oxide has a porosity and has a nano scale structure having a fibrous, wire-like, needle-like, film-like object, columnar shape, or a combination thereof.

5. The sample plate of claim 1, wherein the sample to be analyzed forms fragments through photolysis reaction by ultraviolet irradiation exposed to the photoreaction catalyst layer, and mass analysis of the fragments is performed.

6. The sample plate of claim 1, wherein the surface of the substrate includes a pattern formed by polishing the substrate for increasing the area of the surface.

7. A sample plate for laser desorption/ionization mass spectrometry comprising,
    a substrate comprising a photoreaction catalyst layer on a surface of the substrate, the photoreaction catalyst layer comprising a metal oxide of the same metal as the substrate,
    wherein the photoreaction catalyst layer is formed by corrosion of a metal on the surface of the substrate creating the metal oxide,
    wherein the surface of the substrate includes a unidirectional stripe pattern or a crossing stripe pattern, and a surface roughness and a surface area of the surface corrosion layer is increased by the uni-directional stripe pattern or the crossing stripe pattern, and
    wherein a sample to be analyzed is disposed on the photoreaction catalyst layer.

* * * * *